US012742200B2

(12) United States Patent
Zheng

(10) Patent No.: US 12,742,200 B2
(45) Date of Patent: Sep. 22, 2026

(54) DNA-FISH METHOD FOR MEASUREMENT OF TELOMERE LENGTH

(71) Applicant: Georgetown University, Washington, DC (US)

(72) Inventor: Yun-Ling Zheng, Washington, DC (US)

(73) Assignee: Georgetown University, Washington, DC (US)

( * ) Notice: Subject to any disclaimer, the term of this patent is extended or adjusted under 35 U.S.C. 154(b) by 1239 days.

(21) Appl. No.: 17/630,424

(22) PCT Filed: Jul. 30, 2020

(86) PCT No.: PCT/US2020/044171
§ 371 (c)(1),
(2) Date: Jan. 26, 2022

(87) PCT Pub. No.: WO2021/025935
PCT Pub. Date: Feb. 11, 2021

(65) Prior Publication Data

US 2022/0282318 A1 Sep. 8, 2022

Related U.S. Application Data

(60) Provisional application No. 62/882,267, filed on Aug. 2, 2019.

(51) Int. Cl.

| | |
|---|---|
| ***C12Q 1/6841*** | (2018.01) |
| ***C12Q 1/6816*** | (2018.01) |
| ***C12Q 1/6837*** | (2018.01) |
| ***G01N 21/64*** | (2006.01) |
| ***G06T 7/00*** | (2017.01) |

(52) U.S. Cl.
CPC ....... *C12Q 1/6841* (2013.01); *G01N 21/6428* (2013.01); *G01N 21/6458* (2013.01); *G06T 7/0012* (2013.01); *C12Q 1/6816* (2013.01); *C12Q 1/6837* (2013.01); *C12Q 2600/156* (2013.01); *G01N 2021/6439* (2013.01); *G06T 2207/10056* (2013.01); *G06T 2207/10064* (2013.01); *G06T 2207/30072* (2013.01)

(58) Field of Classification Search
CPC ............ C12Q 2525/151; C12Q 1/6816; G01N 21/6428; G06T 2207/30072
See application file for complete search history.

(56) References Cited

U.S. PATENT DOCUMENTS

| | | | |
|---|---|---|---|
| 5,834,193 | A | 11/1998 | Kozlowski et al. |
| 2004/0132080 | A1 | 7/2004 | Kawaguchi et al. |
| 2006/0210980 | A1 | 9/2006 | Cawthon |
| 2014/0287409 | A1 | 9/2014 | Zheng |
| 2017/0023451 | A1 | 1/2017 | Harley |

FOREIGN PATENT DOCUMENTS

| | | | |
|---|---|---|---|
| WO | WO 2013/049038 A1 | 4/2013 | |
| WO | WO-2019040993 A1 * | 3/2019 | ........... C12Q 1/6806 |

OTHER PUBLICATIONS

Zong et al., "Assessing Telomere Length Using Surface Enhanced Raman Scattering," Scientific Reports, Nov. 10, pp. 1-8. (Year: 2014).*
Beh et al., "Fluorescence spectroscopic detection and measurement of single telomere molecules," Nucleic Acids Research, vol. 46, No. 19, e117, pp. 1-11. (Year: 2018).*
Beh et al., Nucleic Acids Research, vol. 46, No. 19, e117, Supplementary Information, pp. 1-20. (Year: 2018).*
Dudley et al., "Measuring absolute expression with microarrays with a calibrated reference sample and an extended signal intensity range," PNAS, May, vol. 99, No. 11, pp. 7554-7559. (Year: 2002).*
Beh et al., "Fluorescence spectroscopic detection and measurement of single telomere molecules", Nucleic Acids Res., Nov. 2, 2018, 46(19): e117, Epublished Jul. 16, 2018.
International Search Report and Written Opinion for PCT International Patent Application No. PCT/US2020/044171, mailed Oct. 28, 2020.

* cited by examiner

*Primary Examiner* — Young J Kim
(74) *Attorney, Agent, or Firm* — Grimes & Yvon LLP

(57) ABSTRACT

Provided are methods and compositions useful for assessing the length of telomeres. The disclosed methods and compositions are amenable to performance as a high-throughput method to assess telomere length (TL) and TL constitution using genomic DNA. Also provided are methods for diagnosing a telomere-related condition or disease in a subject, assessing general health and/or aging of a subject, establishing a relationship between telomere constitution and cancer and/or aging-related disease, assessing exposure to harmful substances and/or stresses of a subject, assessing response to a drug or drugs treatment of a subject, assessing disease risk of a subject, and assessing clinical outcome of a subject who is suffering from a disease/diseases. The methods are useful in studies of individuals and populations.

9 Claims, 4 Drawing Sheets

Specification includes a Sequence Listing.

SEQUENCE LISTING

```
<160> NUMBER OF SEQ ID NOS: 3

<210> SEQ ID NO 1
<211> LENGTH: 72
<212> TYPE: DNA
<213> ORGANISM: Artificial sequence
<220> FEATURE:
<223> OTHER INFORMATION: Synthetic oligonucleotide

<400> SEQUENCE: 1

ttagggttag ggttagggtt agggttaggg ttagggttag ggttagggtt agggttaggg     60

ttagggttag gg                                                         72


<210> SEQ ID NO 2
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2

agtgaattcg agctcggtac                                                 20


<210> SEQ ID NO 3
<211> LENGTH: 19
<212> TYPE: DNA
```

-continued

```
<213> ORGANISM: Artificial sequence
<220> FEATURE:
<223> OTHER INFORMATION: Synthetic oligonucleotide

<400> SEQUENCE: 3

caagcttgca tgcctgcag                                                    19
```

DNA-FISH METHOD FOR MEASUREMENT OF TELOMERE LENGTH

RELATED APPLICATIONS

This application is a 35 U.S.C. § 371 filing of International Patent Application No. PCT/US2020/044171, filed Jul. 30, 2020, which claims the benefit of U.S. Provisional Patent Application No. 62/882,267, filed Aug. 2, 2019, the entire contents of which are incorporated herein by reference.

STATEMENT REGARDING FEDERALLY SPONSORED RESEARCH OR DEVELOPMENT

This invention was made with government support under Grant No. ES031786 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jan. 26, 2022, is named 726491_GUS-027US_ST25.txt and is 971 bytes in size.

FIELD OF THE INVENTION

The instant disclosure pertains to methods and compositions useful for assessing the length of telomeres, which are end-caps of chromosomes that serve to protect chromosomes from degradation during replication. Telomere length has the potential to serve as useful biomarker in fields such as aging (ageing) and cancer.

BACKGROUND OF THE INVENTION

Telomeres are specialized DNA tandem repeats and protein structures that cap the chromosomal ends and protect the chromosomes from degradation by serving as sacrificial bases during each cell replication. The rate of attrition of these tandem repeats is ~50-200 base-pairs (bp) with every cell division. When telomeres become critically short, they trigger DNA checkpoint responses mediated by telomere-associated proteins that prevent further cell replication. Dysfunction of telomeres can take the form of premature shortening, as in many hereditary telomere syndromes such as dyskeratosis congenita, Hoyeraal-Hreidarsson syndrome, and pulmonary fibrosis. Sarek, G. et al. (2015) *Nat. Struct. Mol. Biol.,* 22, 867-874; Armanios, M. et al. (2012) *Nat. Rev. Genet.,* 13, 693-704. Alternatively, dysfunction of telomeres can take the form of lengthening, such as frequently occurs in cancer and is preceded by failure to arrest replication in the presence of critically short telomeres (Murnane, J. P. et al. (2004) *Bioessays,* 26, 1164-1174; Thompson, S. L. et al. (2011) *Chromosome Res.,* 19, 433-444) and the rescue of ensuing cellular crisis by activation of either telomerase (85-90% of tumors) or proteins associated with alternative lengthening of telomeres. This in turn permits the cells to multiply without constraint.

Telomere length (TL) is also of great interest in the context of the aging process. However, results from studies using TL to test a host of hypotheses related to the biology of human aging have often been inconsistent. In using average TL as the only parameter, these studies fail to take into account the heterogeneity of TLs on chromosome arms, first reported by Lansdorp et al. (1996) *Hum. Mol. Genet.,* 5, 685-691. In fact, it is increasingly recognized that the deleterious effects of telomere dysfunction are mediated by the load of critically short telomeres.

For example, genetic studies in mice have shown that the shortest telomeres, rather than the average TL, are critical for chromosome stability and cell viability, and are likely a major cause of age-related pathologies. Hemann, M. et al. (2001) *Cell,* 107, 67-77. This load can increase due to the gradual shortening of telomeres across all chromosomal arms during normal cellular aging. However, even without significant differences in average TL, the load of critically short telomeres between samples can differ significantly due to variations in the shape of the TL distribution, either between individuals or cell types, or because of bi- or multi-modal distribution that may occur as a result of catastrophic telomere loss, or species-specific telomere biology. Therefore, determining the distribution of absolute TLs is of great importance.

A number of methods for measuring telomere length have been reported. These include cell-based methods and DNA-based methods. All of these methods suffer from certain limitations.

Cell-based methods include quantitative FISH (Q-FISH) (Aubert, G. et al. (2012) *Mut. Res./Fundam. Mol. Mech. Mutagen.,* 730, 59-67) and flow-fluorescence in situ hybridization (FlowFISH) (Aubert, G. et al. (2012) *Mut. Res./Fundam. Mol. Mech. Mutagen.,* 730, 59-67; Aubert, G. et al. (2008) *Physiol. Rev.,* 88, 557-579. 26; Aubert, G. et al. (2012) *PLoS Genet.,* 8, e1002696).

DNA-based methods include quantitative polymerase chain reaction (Q-PCR) methods (Walsh, K. M. et al. (2014) *Nat. Genet.,* 46, 731-735. 24; Codd, V. et al. (2013) *Nat. Genet.,* 45, 422-427), terminal restriction fragments (TRF)/Southern blot analysis (Kimura, M. et al. (2010) *Nat. Protoc.,* 5, 1596-1607; Oexle, K. (1998) *J. Theor. Biol.,* 190, 369-377), another PCR-based approach known as single telomere length analysis (STELA) (Baird, D. M. et al. (2003) *Nat. Genet.,* 33, 203-207), and peptide nucleic acid (PNA) hybridization and analysis of single telomere (PHAST) assay (Beh, C. W. et al. (2018) *Nucleic Acids Res.,* 46, e117).

Metaphase Q-FISH is able to provide an abundance of information, including chromosomal arm-specific TL, however, the method requires cells that can be induced into metaphase, and thus precludes its application to archival samples such as frozen DNA samples. Furthermore, sample preparation is very time consuming and labor intensive, thus severely limiting its practical applications.

The Q-PCR method was first described in 2002 (Cawthon, R. M. (2002) *Nucleic Acids Res.,* 30, e47), and an improved version of monochrome multiplex Q-PCR (MMQ-PCR) was described in 2009 (Cawthon, R. M. (2009) *Nucleic Acids Res.,* 30, e21). The Q-PCR methods have been rapidly adopted in large population studies due to its high-throughput, low-cost nature and the requirement of only a small amount of DNA. However, emerging data have generated concerns about the validity and reliability of this method for accurate TL measurement. Since the rapid adoption Q-PCR method in population studies, large technique variations have been reported. Martin-Ruiz, C. M et al. (2015) *Int J Epidemiol.,* 44, 1673-1683. Self-reported indicators of reproducibility, measured as inter-batch coefficients of variation (CV), differ widely between laboratories, ranging from 4% to 61%.

Despite their high sensitivity, quantitative polymerase chain reaction (qPCR) methods using primers specific to the telomere repeat sequence yield only average TL for a given sample. Despite the low-cost and high-throughput nature of the qPCR method, this approach (and other extant methods) only estimates average TL. Average TL is not fully informative of TL constitution in cells, because a diploid human cell contains 92 chromosomal ends and TLs at the 92 chromosomal ends are highly heterogeneous. Flow-FISH fluorescently labels telomeres in blood cells that are then analyzed by flow cytometry, and gives the distribution of total TL in each cell. Neither of these methods can detect small fractions of critically short telomeres among all chromosomal ends, arguably the most important telomere biomarker. Although TRF/Southern blot analysis can in principle yield information of the size distribution of telomeres, it is only semiquantitative, with relatively poor sensitivity, particularly for shorter telomeres. Furthermore, the size estimates are skewed by the presence of a sub-telomeric sequence of variable size on each fragment, limiting their utility. STELA is a PCR-based method and uses chromosome-specific primers to amplify telomeres for each chromosomal arm, but fails to capture adequately the complete picture of the TL dynamics within cells since primers exist for less than one-fifth of all chromosomal arms. Another limitation of STELA is difficult to amplify long telomeres. PHAST is a flow-based fluorescence spectroscopic method for measuring TL; while it is highly sensitive, it requires a large amount of DNA and specialized fluorescence spectroscopy equipment that is not commercially available. Because the throughput is low, it is not suitable for large population studies.

Thus, there still exists a need for improved methods of measuring telomere length.

SUMMARY OF THE INVENTION

The instant disclosure provides novel methods and compositions of matter useful for measuring telomere length (TL) and telomere length constitution. In certain embodiments, the methods comprise determining telomere lengths for two or more telomeres; telomere length variation; frequency of short telomeres; and frequency of long telomeres. In certain embodiments, the methods comprise determining telomere length for a single telomere.

Significantly, the methods disclosed herein are amenable to performance as a high-throughput method to assess TL and TL constitution using genomic DNA. Additionally, the methods disclosed herein will find use in performing large population studies and discovery and validation of associations between telomere properties, including TL and TL constitution, and as diagnostic tests for various conditions and diseases with telomere abnormalities, including, for example, aging, bone marrow failure, interstitial lung diseases, and cancer.

An aspect of the present disclosure is a method for determining telomere length, comprising:

a) immobilizing onto a substrate at least one sample of genomic DNA and a plurality of telomere length standards of different lengths;
b) contacting the immobilized genomic DNA and telomere length standards of step a) with a fluorescently labeled probe having a sequence complimentary to a telomere sequence under conditions such that said probe hybridizes specifically to telomeric DNA;
c) detecting hybridized probe with a fluorescent microscopy image system, thereby generating digitized images of signals from the hybridized probe;
d) analyzing the digitized images for spot count and individual spot intensity;
e) generating a standard curve of telomere length in base-pair versus spot fluorescent intensity based on the plurality of telomere length standards;
f) determining at least one of the following for each sample of genomic DNA:
   (i) average telomere length per telomere;
   (ii) telomere length variation (TLV);
   (iii) frequency of short telomeres; and
   (iv) frequency of long telomeres.

In certain embodiments, the genomic DNA is human DNA.

In certain embodiments, the telomere length standards are cloned telomere fragments.

In certain embodiments, the telomere length standards are telomere DNA purified from cells with known telomere length. Such standards are particularly useful for species, such as mice, with long telomeres, e.g. >100 kb.

In certain embodiments, the plurality of telomere length standards of different lengths comprises cloned telomere fragments of about 0.1 to about >=9.0 kb.

In certain embodiments, the plurality of telomere length standards of different lengths comprises telomere DNA purified from cells with long telomeres, for example >9.0 kb.

In certain embodiments, the substrate comprises a glass surface.

In certain embodiments, the substrate consists of glass.

In certain embodiments, the substrate consists of a cover glass.

In certain embodiments, the substrate consists of a multi-well plate, such as a 96-well plate.

In certain embodiments, the fluorescent microscopy image system comprises a digital camera, such as a charge-coupled device (CCD) or complementary metal oxide semiconductor (CMOS) camera.

In certain embodiments, fluorescent intensity is determined for each telomere.

In certain embodiments, fluorescent intensities are converted to base-pair length for each telomere by linear regression against the standard curve.

In certain embodiments, step f) comprises determining each of the following for each sample of genomic DNA:

(i) average length per telomere;
(ii) telomere length variation;
(iii) frequency of short telomeres; and
(iv) frequency of long telomeres.

In certain embodiments, the short telomeres are less than or equal to about 1 kb long.

In certain embodiments, the long telomeres are greater than or equal to about 15 kb long.

In certain embodiments, about 1000-10,000 telomeres are measured for each sample of genomic DNA.

In certain embodiments, about 3000 telomeres are measured for each sample of genomic DNA.

In certain embodiments, the at least one sample of genomic DNA comprises DNA isolated from one or more tissue obtained from a subject, wherein the tissue is selected from the group consisting of blood, bone marrow, skin, bone, muscle, heart, blood vessel, lung, prostate, breast, colon, rectum, kidney, bladder, lymph node, thyroid, uterus, ovary, brain, tongue, mouth, esophagus, stomach, liver, spleen, pancreas, small intestine, and cervix.

In certain embodiments, the at least one sample of genomic DNA comprises DNA isolated from one or more cell type obtained from a subject, wherein the cell type is selected from the group consisting of buffy coat, peripheral blood mononuclear cells (PBMCs), lymphocytes, monocytes, granulocytes, and any combination thereof.

In certain embodiments, the at least one sample of genomic DNA comprises DNA isolated from a tumor obtained from a subject.

In certain embodiments, the at least one sample of genomic DNA comprises DNA isolated from one or more cell type obtained from a subject, wherein the cell type is present in or derived from a body fluid, e.g., urine, saliva, or sputum.

In certain embodiments, the at least one sample of genomic DNA comprises DNA isolated from one or more cell type obtained from a subject, wherein the cell type is present in or derived from an organ or tissue of the subject.

In certain embodiments, the at least one sample of genomic DNA comprises DNA isolated from one or more cell type obtained from a subject, wherein the cell type is selected from the group consisting of circulating tumor cells, circulating stem cells, and any combination thereof.

In certain embodiments, the at least one sample of genomic DNA comprises DNA isolated from one or more cell type obtained from a subject, wherein the cell type is selected from the group consisting of urine, buccal cells, salivary, sputum, organ tissues and any combination thereof.

An aspect of the present disclosure is a substrate comprising a surface onto which a plurality of telomere length standards of different lengths is immobilized.

In certain embodiments, the telomere length standards are cloned telomere fragments.

In certain embodiments, the telomere length standards are telomere DNA purified from cells with known telomere lengths.

In certain embodiments, the plurality of telomere length standards of different lengths comprises cloned telomere fragments of about 0.1 to about 9.0 kb.

In certain embodiments, the plurality of telomere length standards of different lengths comprises telomere DNA purified from cells with long telomeres, for example >9.0 kb.

In certain embodiments, the plurality of telomere length standards of different lengths comprises telomere lengths of about 0.1 to about 2.4 kb.

In certain embodiments, the substrate further comprises at least one sample of genomic DNA immobilized onto the surface.

In certain embodiments, the at least one sample of genomic DNA comprises DNA isolated from one or more tissue obtained from a subject, wherein the tissue is selected from the group consisting of blood, bone marrow, skin, bone, muscle, heart, blood vessel, lung, prostate, breast, colon, rectum, kidney, bladder, lymph node, thyroid, uterus, ovary, brain, tongue, mouth, esophagus, stomach, liver, spleen, pancreas, small intestine, and cervix.

In certain embodiments, the at least one sample of genomic DNA comprises DNA isolated from one or more cell type obtained from a subject, wherein the cell type is selected from the group consisting of blood cell, bone marrow cell, skin cell, bone cell, muscle cell, heart cell, blood vessel cell, lung cell, prostate cell, breast cell, colon cell, rectum cell, kidney cell, bladder cell, lymph node cell, thyroid cell, uterus cell, ovary cell, brain cell, tongue cell, mouth cell, esophagus cell, stomach cell, liver cell, spleen cell, pancreas cell, small intestine cell, and cervix cell.

In certain embodiments, the at least one sample of genomic DNA comprises DNA isolated from one or more cell type obtained from a subject, wherein the cell type is selected from the group consisting of buffy coat, peripheral blood mononuclear cells (PBMCs), lymphocytes, monocytes, granulocytes, and any combination thereof.

In certain embodiments, at least one sample of genomic DNA comprises DNA isolated from a tumor obtained from a subject.

In certain embodiments, the at least one sample of genomic DNA comprises DNA isolated from one or more cell type obtained from a subject, wherein the cell type is selected from the group consisting of tumor cells, stem cells, and any combination thereof.

In certain embodiments, the at least one sample of genomic DNA comprises DNA isolated from one or more cell type obtained from a subject, wherein the cell type is selected from the group consisting of circulating tumor cells, circulating stem cells, and any combination thereof.

In certain embodiments, the at least one sample of genomic DNA comprises DNA isolated from one or more cell type obtained from a subject, wherein the cell type is selected from the group consisting of salivary cells, urine cells, sputum cells and any combination thereof.

An aspect of the present disclosure is a kit, comprising a plurality of telomere length standards of different lengths.

In certain embodiments, the telomere length standards are cloned telomere fragments or telomere DNAs purified from cells with known telomere length.

In certain embodiments, the plurality of telomere length standards of different lengths comprises telomere lengths of about 0.1 to about 9.0 kb.

In certain embodiments, the plurality of telomere length standards of different lengths comprises telomere DNA purified from cells with long telomeres, for example >9.0 kb.

In certain embodiments, the kit further comprises a DNA binding buffer and a hybridization buffer.

In certain embodiments, the kit further comprises a fluorescently labeled probe having a sequence complimentary to a telomere sequence.

An aspect of the present disclosure is a method for diagnosing a telomere-related condition or disease in a subject, comprising:

a) obtaining a biological sample from a subject;
b) immobilizing onto a substrate at least one sample of genomic DNA derived from the biological sample and a plurality of telomere length standards of different lengths;
c) contacting the immobilized genomic DNA and plurality of telomere length standards of different lengths of step b) with a fluorescently labeled probe having a sequence complimentary to a telomere sequence under conditions such that said probe hybridizes specifically to telomeric DNA;
d) detecting hybridized probe with a fluorescent microscopy image system, thereby generating a digitized image of the hybridized probe;
e) analyzing the digitized image for spot count and individual spot fluorescent intensity;
f) generating a standard curve of base-pair telomere length versus spot fluorescent intensities based on the plurality of telomere length standards on the substrate;
g) determining at least one of the following for each sample of genomic DNA:
(i) average telomere length per telomere;
(ii) telomere length variation (TLV);
(iii) frequency of short telomeres; and
(iv) frequency of long telomeres; and
h) diagnosing the subject as having the telomere-related condition or disease based on the information obtained in step g).

An aspect of the present disclosure is a method for assessing general health and/or aging of a subject, comprising:

a) obtaining a biological sample from a subject;

b) immobilizing onto a substrate at least one sample of genomic DNA derived from the biological sample and a plurality of telomere length standards of different lengths;

c) contacting the immobilized genomic DNA and plurality of telomere length standards of different lengths of step b) with a fluorescently labeled probe having a sequence complimentary to a telomere sequence under conditions such that said probe hybridizes specifically to telomeric DNA;

d) detecting hybridized probe with a fluorescent microscopy image system, thereby generating digitized images of the hybridized probe;

e) analyzing the digitized s for spot count and individual spot intensity;

f) generating a standard curve of base-pair telomere length versus spot fluorescent intensities based on the plurality of telomere length standards;

g) determining at least one of the following for each sample of genomic DNA:

(i) average telomere length per telomere;

(ii) telomere length variation (TLV);

(iii) frequency of short telomeres; and (iv) frequency of long telomeres; and h) identifying the subject as having normal or abnormal general health and/or aging based on the information obtained in step g).

An aspect of the present disclosure is a method for establishing a relationship between telomere constitution and cancer and/or aging-related disease, comprising:

a) obtaining a biological sample from each of a population of subjects;

b) immobilizing onto a substrate at least one sample of genomic DNA derived from the biological sample and a plurality of telomere length standards of different lengths;

c) contacting the immobilized genomic DNA and plurality of telomere length standards of different lengths of step b) with a fluorescently labeled probe having a sequence complimentary to a telomere sequence under conditions such that said probe hybridizes specifically to telomeric DNA;

d) detecting hybridized probe with a fluorescent microscopy image system, thereby generating digitized images of the hybridized probe;

e) analyzing the digitized images for spot count and individual spot intensity;

f) generating a standard curve of base-pair telomere length versus spot fluorescent intensities based on the plurality of telomere length standards;

g) determining at least one of the following for each sample of genomic DNA:

(i) average telomere length per telomere;

(ii) telomere length variation (TLV);

(iii) frequency of short telomeres; and (iv) frequency of long telomeres; and h) identifying a relationship between telomere constitution and cancer and/or aging-related disease based on the information obtained in step g).

An aspect of the present disclosure is a method for assessing exposure to harmful substances and/or stresses of a subject, comprising:

a) obtaining a biological sample from a subject;

b) immobilizing onto a substrate at least one sample of genomic DNA derived from the biological sample and a plurality of telomere length standards of different lengths;

c) contacting the immobilized genomic DNA and plurality of telomere length standards of different lengths of step b) with a fluorescently labeled probe having a sequence complimentary to a telomere sequence under conditions such that said probe hybridizes specifically to telomeric DNA;

d) detecting hybridized probe with a fluorescent microscopy image system, thereby generating digitized images of the hybridized probe;

e) analyzing the digitized images for spot count and individual spot fluorescent intensity;

f) generating a standard curve of telomere length in base-pair versus spot fluorescent intensities based on the plurality of telomere length standards on the substrate;

g) determining at least one of the following for each sample of genomic DNA:

(i) average telomere length per telomere;

(ii) telomere length variation (TLV);

(iii) frequency of short telomeres; and (iv) frequency of long telomeres; and h) identifying the subject as having harmful exposure or not based on the information obtained in step g).

An aspect of the present disclosure is a method for assessing response to a drug or drugs treatment of a subject, comprising:

a) obtaining a biological sample from a subject;

b) immobilizing onto a substrate at least one sample of genomic DNA derived from the biological sample and a plurality of telomere length standards of different lengths;

c) contacting the immobilized genomic DNA and plurality of telomere length standards of different lengths of step b) with a fluorescently labeled probe having a sequence complimentary to a telomere sequence under conditions such that said probe hybridizes specifically to telomeric DNA;

d) detecting hybridized probe with a fluorescent microscopy image system, thereby generating digitized images of the hybridized probe;

e) analyzing the digitized images for spot count and individual spot fluorescent intensity;

f) generating a standard curve of telomere length in base-pair versus spot fluorescent intensities based on the plurality of telomere length standards on the substrate;

g) determining at least one of the following for each sample of genomic DNA:

(i) average telomere length per telomere;

(ii) telomere length variation (TLV);

(iii) frequency of short telomeres; and (iv) frequency of long telomeres; and h) determining the effect of the drug/drugs on the subject based on the information obtained in step g).

An aspect of the present disclosure is a method for assessing disease risk of a subject, comprising:

a) obtaining a biological sample from a subject;
b) immobilizing onto a substrate at least one sample of genomic DNA derived from the biological sample and a plurality of telomere length standards of different lengths;
c) contacting the immobilized genomic DNA and plurality of telomere length standards of different lengths of step b) with a fluorescently labeled probe having a sequence complimentary to a telomere sequence under conditions such that said probe hybridizes specifically to telomeric DNA;
d) detecting hybridized probe with a fluorescent microscopy image system, thereby generating digitized images of the hybridized probe;
e) analyzing the digitized images for spot count and individual spot fluorescent intensity;
f) generating a standard curve of telomere length in base-pair versus spot fluorescent intensities based on the plurality of telomere length standards on the substrate;
g) determining at least one of the following for each sample of genomic DNA:
   (i) average telomere length per telomere;
   (ii) telomere length variation (TLV);
   (iii) frequency of short telomeres; and
   (iv) frequency of long telomeres; and
h) determining the subject's risk category for a disease/diseases based on the information obtained in step g).

An aspect of the present disclosure is a method for assessing clinical outcome of a subject who is suffering from a disease/diseases, comprising:

a) obtaining a biological sample from a subject;
b) immobilizing onto a substrate at least one sample of genomic DNA derived from the biological sample and a plurality of telomere length standards of different lengths;
c) contacting the immobilized genomic DNA and plurality of telomere length standards of different lengths of step b) with a fluorescently labeled probe having a sequence complimentary to a telomere sequence under conditions such that said probe hybridizes specifically to telomeric DNA;
d) detecting hybridized probe with a fluorescent microscopy image system, thereby generating digitized images of the hybridized probe;
e) analyzing the digitized images for spot count and individual spot fluorescent intensity;
f) generating a standard curve of telomere length in base-pair versus spot fluorescent intensities based on the plurality of telomere length standards on the substrate;
g) determining at least one of the following for each sample of genomic DNA:
   (i) average telomere length per telomere;
   (ii) telomere length variation (TLV);
   (iii) frequency of short telomeres; and
   (iv) frequency of long telomeres; and
h) determining the likelihood of survival/recovery from the disease/diseases of the subject based on the information obtained in step g).

DETAILED DESCRIPTION OF THE INVENTION

Figure 1A:
FIG. 1A is a photographic image depicting DNA-FISH of human genomic DNA purified from blood leukocytes. Shown is green fluorescent image of DNA stained with YoYo-1, a DNA binding dye. Image was obtained under a 100× oil objective.

In accordance with the instant disclosure, a high resolution and sensitive method (termed DNA-FISH) that can measure the lengths of single telomeres is provided that advances the field by its ability to assess multiple aspects of telomere constitution, not just average telomere length (TL). For example, while average TL measured by qPCR generated contradictory results regarding the association between TL in blood leukocytes and cancer risk, high telomere length variation (TLV), measured by metaphase-FISH, has been shown to be consistently associated with an increased risk of breast, lung and bladder cancers. Further, TLV plus average TL enhanced cancer risk prediction over average TL alone. Moreover, we found that short TLs on certain chromosomal ends were significantly associated with risk of breast cancer (Zheng Y. L. et al. (2009) *Carcinogenesis,* 30, 1380-1386; Zheng, Y. L. et al. (2011) *Hum. Mol. Genet.,* 20, 378-386), potentially providing information to guide investigations on the role of specific genes and pathways related to these chromosomes. The instant disclosure highlights the value of using multiple telomere parameters to assess TL constitution and illustrates the potential benefits of measuring the lengths of single telomeres on specific chromosomes.

As disclosed herein, DNA-FISH is a method for the measurement of absolute length of each individual telomere using a small amount (e.g., 100 ng) of genomic DNA. The method is relatively inexpensive and is well suited for high-throughput use. The method is capable of rapidly measuring the lengths of thousands of telomeres (e.g., 3000) with high sensitivity from each DNA sample and generate 4 telomere parameters: 1) average TL per telomere; 2) telomere length variation (TLV), defined as coefficient of variation (CV) of mean TL among all measured telomeres; 3) frequency of short telomeres (e.g., percentage of telomeres ≤1 kb in length); and 4) frequency of long telomeres (e.g.

percentage of telomeres ≥15 kb in length). These 4 parameters provide a depiction of not only telomere lengths but also length distributions, and are improved telomere biomarkers to delineate the relationships between telomere characteristics and environmental exposures, psychosocial stress, aging, and disease susceptibility.

As used herein, the term "telomere" means a region of repetitive nucleotide sequences at each end of a chromosome, which protects the end of the chromosome from deterioration or from fusion with neighboring chromosomes. For vertebrates, the sequence of nucleotides in telomeres is AGGGTT with the complementary DNA strand being TCC-CAA, with a single-stranded TTAGGG overhang. This sequence of TTAGGG is repeated approximately 2,500 times in humans. In humans, average telomere length declines from about 11 kilobases (kb) at birth to fewer than 4 kilobases iii old age, with the average rate of decline being greater in men than in women. During chromosome replication, the enzymes that duplicate DNA cannot continue their duplication all the way to the end of a chromosome, so in each duplication the end of the chromosome is shortened.

As used herein, the term "telomeric constitution" means distribution or composition of telomere lengths As used herein, the term "telomeric DNA" means the DNA found in a telomere.

As used herein, the term "telomeric length" or, equivalently, "TL," means the number of basepairs of telomeric DNA in a telomere. In some embodiments, the length or number of basepairs can be exact. In some embodiments, the length or number of basepairs can be an approximation. For example, a telomeric length can be a specified length ±0.1 kb.

As used herein, the term "telomere length variation" or, equivalently, "TLV," means the coefficient of variation of mean telomere length among all measured telomeres.

As used herein, the term "long telomere" means a telomere length of greater than or equal to about 11 kb. In certain embodiments, a long telomere is greater than or equal to about 15 kb long. In certain embodiments, a long telomere is greater than 15 kb long.

As used herein, the term "short telomere" means a telomere length of less than or equal to about 4 kb. In certain embodiments, a short telomere is less than or equal to about 1 kb long. In certain embodiments, a short telomere is less than 1 kb long.

As used herein, the term "telomeric region" means the double-stranded DNA segment at the ends of a chromosome with repeat telomeric sequence (TTAGGG:CCCTAA repeats).

As used herein, the term "sub-telomeric region" means the segment of DNA immediately adjacent to telomere at the centromeric side of telomeres. A sub-telomeric region often contains degenerate telomeric repeats. In the case of humans, repeats of TGAGGG and TCAGGG can be present in the sub-telomeric region.

As used herein, the term "genomic DNA" means chromosomal DNA. Genomic DNA can optionally include one or more proteins, e.g., histones, naturally associated with DNA in chromatin.

As used herein, the terms "hybridize" and "hybridization" mean the formation of a duplex structure by two single-stranded nucleic acids due to complementary base pairing. Hybridization can occur between fully complementary nucleic acid strands or between "substantially complementary" nucleic acid strands that contain minor regions of mismatch. Conditions under which only fully complementary nucleic acid strands will hybridize are referred to as "stringent hybridization conditions" or "sequence-specific hybridization conditions". Stable duplexes of substantially complementary sequences can be achieved under less stringent hybridization conditions; the degree of mismatch tolerated can be controlled by suitable adjustment of the hybridization conditions. Those skilled in the art of nucleic acid technology can determine duplex stability empirically considering a number of variables including, for example, the length and base pair composition of the oligonucleotides, ionic strength, and incidence of mismatched base pairs, following the guidance provided by the art (see, e.g., Sambrook et al., (1989) Molecular Cloning—A Laboratory Manual (Cold Spring Harbor Laboratory, Cold Spring Harbor, N.Y.); and Wetmur (1991) Crit Rev Biochem Mol Biol. 26(3-4):227-259; both incorporated herein by reference).

As used herein, the terms "immobilize" or "immobilizing" mean physically or chemically adhere or physically or chemically adhering a substance of interest to a substrate. For example, a sample of genomic DNA can be immobilized onto a substrate.

As used herein, the term "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, the term "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, the term "probe" means a substance that is capable of interacting with a substance of interest. In certain embodiments, a probe can comprise a nucleic acid having a sequence that is complementary to a nucleic acid of interest. In certain embodiments, a probe can comprise a nucleic acid, e.g., an oligonucleotide, conjugated to a detectable label. In certain embodiments, a probe can comprise a nucleic acid, e.g., an oligonucleotide, conjugated to a fluorophore, e.g., fluorescein isothiocyanate (FITC), Cy3B, Cy3.5, Cy5, and others well known and commercially available from various suppliers.

Examples of additional suitable fluorescent labels include, but are not limited to, SYBR Green I (Invitrogen), 5,6-carboxymethyl fluorescein, Texas red, nitrobenz-2-oxa-1,3-diazol-4-yl (NBD), coumarin, dansyl chloride, rhodamine, amino-methyl coumarin (AMCA), Eosin, Erythrosin, BODIPY®, Cascade Blue®, Oregon Green®, pyrene, lissamine, xanthenes, acridines, oxazines, phycoerythrin, macrocyclic chelates of lanthanide ions such as Quantum Dye™, fluorescent energy transfer dyes, such as thiazole orange-ethidium heterodimer, and the cyanine dyes Cy3, Cy3.5, Cy5, Cy5.5 and Cy7. Examples of other specific fluorescent labels include 3-Hydroxypyrene 5,8,10-Tri Sulfonic acid, 5-Hydroxy Tryptamine (5-HT), Acid Fuchsin, Alizarin Complexon, Alizarin Red, Allophycocyanin, Aminocoumarin, Anthroyl Stearate, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxa-diazole), BCECF, Berberine Sulphate, Bisbenzamide, Blancophor FFG Solution, Blancophor SV, Bodipy F1, Brilliant Sulphoflavin FF, Calcien Blue, Calcium Green, Calcofluor RW Solution, Calcofluor White, Calcophor White ABT Solution, Calcophor White Standard Solution, Carbostyryl, Cascade Yellow, Catecholamine, Chinacrine, Coriphosphine O, Coumarin-Phalloidin, CY3.1 8, CY5.1 8, CY7, Dans (1-Dimethyl Amino Naphaline 5 Sulphonic Acid), Dansa (Diamino Naphthyl Sulphonic Acid), Dansyl NH—CH3, Diamino Phenyl Oxydiazole (DAO), Dimethylamino-5-Sulphonic acid, Dipyrrometheneboron Difluoride, Diphenyl Brilliant Flavine 7GFF, Dopamine, Erythrosin ITC, Euchrysin, FIF (Formaldehyde Induced Fluorescence), Flazo Orange, Fluo 3, Fluorescamine, Fura-2, Genacryl Brilliant Red B, Genacryl Brilliant Yellow 10GF, Genacryl Pink 3G, Genacryl Yellow SGF, Gloxalic Acid, Granular Blue, Haematoporphyrin, Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Marina Blue, Maxilon Brilliant Flavin 10 GFF, Maxilon Brilliant Flavin 8 GFF, MPS (Methyl Green Pyronine Stilbene), Mithramycin, NBD Amine, Nitrobenzoxadidole, Noradrenaline, Nuclear Fast Red, Nuclear Yellow, Nylosan Brilliant Flavin EBG, Oxadiazole, Pacific Blue, Pararosaniline (Feulgen), Phorwite AR Solution, Phorwite BKL, Phorwite Rev, Phorwite RPA, Phosphine 3R, Phthalocyanine, Phycoerythrin R, Polyazaindacene Pontochrome Blue Black, Porphyrin, Primuline, Procion Yellow, Pyronine, Pyronine B, Pyrozal Brilliant Flavin 7GF, Quinacrine Mustard, Rhodamine 123, Rhodamine 5 GLD, Rhodamine 6G, Rhodamine B, Rhodamine B 200, Rhodamine B Extra, Rhodamine BB, Rhodamine BG, Rhodamine WT, Serotonin, Sevron Brilliant Red 2B, Sevron Brilliant Red 4G, Sevron Brilliant Red B, Sevron Orange, Sevron Yellow L, SITS (Primuline), SITS (Stilbene Isothiosulphonic acid), Stilbene, Snarf 1, sulpho Rhodamine B Can C, Sulpho Rhodamine G Extra, Tetracycline, Thiazine Red R, Thioflavin S, Thioflavin TCN, Thioflavin 5, Thiolyte, Thiozol Orange, Tinopol CBS, True Blue, Ultralite, Uranine B, Uvitex SFC, Xylene Orange, and XRITC.

As used herein, the term "subject" can be a vertebrate, such as a mammal, a fish, a bird, a reptile, or an amphibian. Thus, the subject of the herein disclosed methods can be a human, non-human primate, horse, cow, pig, sheep, goat, dog, cat, rabbit, guinea pig, or rodent. The term does not denote a particular age or sex. Thus, adult and newborn subjects, as well as fetuses, whether male or female, are intended to be covered. In certain embodiments, the subject is a mammal. In certain embodiments, the subject is a human. A patient refers to a subject afflicted with a condition, disease or disorder. The term "patient" includes human and veterinary subjects. In some embodiments of the disclosed methods, the subject has been diagnosed with a need for treatment of one or more conditions or diseases associated with altered telomere length or an altered telomere length constitution. For example, a subject with a particular clinical condition can have cells with chromosomes having an altered telomere length or an altered telomere length constitution resulting from a dysfunction in telomerase activity. In such conditions, the dysfunction in telomerase activity leads to critically short telomeres ("telomere disease").

As used herein, the term "substrate" refers to a material or surface onto which a material can be immobilized. In certain embodiments, a substrate is made of glass, e.g., a glass microscope slide or a cover glass. In certain embodiments, a substrate can be in the form of a multiwell plate, e.g., a 96-well or 384-well plate.

As used herein, the term "telomere-related condition or disease" means any condition or disease that has an association or has been associated with abnormal telomere length and/or other telomere characteristic. Such conditions and diseases include, without limitation, aging, certain congenital syndromes, cancer, cardiovascular disease, diabetes mellitus (viz., type 1 diabetes and type 2 diabetes), cirrhosis, infection with human immunodeficiency virus (HIV), Hutchinson Gilford progeria, dyskeratosis congenita, idiopathic pulmonary fibrosis, aplastic anemia.

In one aspect, the present disclosure finds use in the assessment and monitoring of cardiovascular disease. Telomere length in white blood cells has been shown to be shorter in patients with severe triple vessel coronary artery disease than it is in individuals with normal coronary arteries as determined by angiography (Samani, N. J. et al., Lancet, 2001, 358:472-73), and also in patients who experiencing a premature myocardial infarction before age 50 years as compared with age- and sex-matched individuals without such a history (Brouilette S. et al., Arterioscler. Thromb. Vasc. Biol., 2003, 23:842-46). Brouilette et al. (Lancet, 2007, 369:107-14) has suggested that shorter leucocyte telomeres in people prone to coronary heart disease could indicate the cumulative effect of other cardiovascular risk factors on telomere length. Increased oxidative stress also contributes to atherosclerosis, and increased oxidant stress has been shown to increase rates of telomere attrition in vitro (Harrison, D., Can. J. Cardiol., 1998, 14(suppl D):30D-32D; von Zglinicki, T., Ann. N. Y. Acad. Sci., 2000, 908:99-110).

In cross-sectional studies, smoking, body-mass index, and type 1 diabetes mellitus have also been reported to be associated with shorter leucocyte telomere length (Valdes, A., et al., Lancet, 2005, 366:662-64; Jeanclos, E. et al., Diabetes, 1998, 47:482-86). Increased life stress, a factor known to increase the risk of coronary heart disease, has been shown to be associated with shorter telomeres, possibly as a consequence of increased oxidative stress (Epel, E. S. et al., Proc. Natl. Acad. Sci. USA, 2004, 49:17312-15). Thus, smokers and patients with a high body-mass index, diabetes and/or increased life stress would all benefit from determination and continued monitoring of their telomere abundance according to the method of the disclosure.

Type 2 diabetes is characterized by shorter telomeres (Salpea, K. and Humphries, S. E., Atherosclerosis, 2010, 209(1):35-38). Shorter telomeres have also been observed in type 1 diabetes patients (Uziel O. et al., Exper. Gerontology, 2007, 42:971-978). The etiology of the disease in type 1 diabetes is somewhat different from that in type 2, although in both cases, beta cell failure is the final trigger for full-blown disease. Telomere length is thus a useful marker for diabetes since it is associated with the disease progression. Adaikalakoteswari et al. (Atherosclerosis, 2007, 195: 83-89) have shown that telomeres are shorter in patients with pre-diabetic impaired glucose tolerance compared to controls. In addition, telomere shortening has been linked to diabetes complications, such as diabetic nephropathy (Verzola D. et al., Am. J. Physiol., 2008, 295:F1563-1573), microalbuminuria (Tentolouris, N. et al., Diabetes Care, 2007, 30:2909-2915), and epithelial cancers (Sampson, M. J. et al., Diabetologia, 2006, 49:1726-1731) while telomere shortening seems to be attenuated in patients with well-controlled diabetes (Uziel, 2007, ibid.). The method of the present disclosure is particularly useful in monitoring the status of pre-diabetic and diabetic patients to provide an early warning for these complications and others.

The present disclosure is useful for determining telomere lengths of various types of cancer cells because activation of telomerase activity is associated with immortalization of cells. While normal human somatic cells do not or only transiently express telomerase and therefore shorten their telomeres with each cell division, most human cancer cells typically express high levels of telomerase and show unlimited cell proliferation. High telomerase expression allows cells to proliferate and expand long term and therefore supports tumor growth (Roth, A. et al., in Small Molecules in Oncology, Recent Results in Cancer Research, U. M. Martens (ed.), Springer Verlag, 2010, pp. 221-234). Shorter telomeres are significantly associated with risk of cancer, especially cancers of the bladder and lung, smoking-related, the digestive system and the urogenital system. Excessive telomere shortening likely plays a role in accelerating tumor onset and progression (Ma H. et al., PLoS ONE, 2011, 6(6): e20466. doi:10.1371/journal.pone.0020466). Studies have further shown that the effect of shortened telomeres on breast cancer risk is significant for certain population subgroups, such as premenopausal women and women with a poor anti-oxidative capacity (Shen J., et al., Int. J. Cancer, 2009, 124:1637-1643). In addition to the assessing and monitoring cancers in general, the present disclosure is particularly useful for the monitoring of oral cancers if genomic DNA derived from saliva samples is utilized.

Cirrhosis of the liver is characterized by increasing fibrosis of the organ often associated with significant inflammatory infiltration. Wiemann et al. (FASEB Journal, 2002, 16(9):935-982) have shown that telomere shortening is a disease- and age-independent sign of liver cirrhosis in humans. Telomere shortening is present in cirrhosis induced by viral hepatitis (chronic hepatitis A and B), toxic liver damage (alcoholism), autoimmunity, and cholestasis (PBC and PSC); telomeres are uniformly short in cirrhosis independent of the age of the patients. Telomere shortening and senescence specifically affect hepatocytes in the cirrhotic liver and both parameters strongly correlate with progression of fibrosis during cirrhosis. Thus, the method of the present disclosure finds use in diagnosing and monitoring liver fibrosis.

Depression has been likened to a state of "accelerated aging," and depressed individuals have a higher incidence of various diseases of aging, such as cardiovascular and cerebrovascular diseases, metabolic syndrome, and dementia. People with recurrent depressions or those exposed to chronic stress exhibit shorter telomeres in white blood cells. Shorter telomere length is associated with both recurrent depression and cortisol levels indicative of exposure to chronic stress (Wikgren, M. et al., Biol. Psych., 2011, DOI: 10.1016/j.biopsych.2011.09.015). However, not all depressed individuals show shortened telomeres equally because of a large variance in depressive episodes over a lifetime. Those who suffered from depression for long durations have significantly shorter telomeres due to longer exposure to oxidative stress and inflammation induced by psychological stress when compared with control populations (Wolkowitz et al., PLoS One, 2011, 6(3):e17837). Thus, the method of the present disclosure may find use in monitoring depression.

Abnormal telomere length in blood leukocytes is associated with chronic infection including HIV (Effros R B et al, AIDS. 1996 July; 10(8):F17-22, Pommier et al Virology. 1997, 231(1):148-54), and HBV, HCV and CMV (Telomere/telomerase dynamics within the human immune system: effect of chronic infection and stress. (Effros, R. B., Exp Gerontol. 2011 46(2-3):135-40; Harley, C. B. et al., Rejuvenation Res. 2011 February; 14(1):45-56. doi: 10.1089rej.2010.1085)

In Harley et al., Rejuvenation Res., 2011, 14(1):45-56, it was found that individuals who were CMV seropositive had shorter telomeres than those who were CMV negative, and moreover, the CMV positive subjects were more likely to respond to a nutritional supplement program of TA-65, a natural product-derived telomerase activator along with other supplements, in reducing the abundance of senescent CD8+/CD28− cells, suggesting a companion diagnostics application for measuring average telomere length or abundance of short telomeres, in conjunction with administration of telomerase activators or other agents that lead to longer telomeres.

Measurement of average telomere length can be used as indicator of prognosis disease progression and treatment outcome.

One study reported that telomere length in CD4+ cells is related to inflammatory grade, fibrosis stage, laboratory indices of severity, subsequent hepatic decompensation and treatment outcome in patients with chronic HCV infection (Hoare et al., J. Hepatol., 2010, 53(2):252-260).

In another report, longer leukocyte telomere length predicts increased risk of hepatitis B virus-related hepatocellular carcinoma (Liu et al, 2011, 117(18):4247-56).

In the case of HIV, telomere shortening is caused by viral infection. In addition, the nucleoside analog reverse-transcriptase inhibitors used to treat HIV are telomerase inhibitors (Strahl and Blackburn, Mol Cell Biol., 1996, 16(1):53-65; Hukezalie et al, PLoS One, 2012, 7(11):e47505). Measurement of short telomere abundance might help determine the side effects and efficacy of HAART treatment.

The present disclosure also finds use in diagnosis of diseases related to early onset of aging. For example, individuals with Hutchinson Gilford progeria disease show premature aging and reduction in proliferative potential in fibroblasts associated with loss of telomeric length (Allsopp, R. C. et al, Proc. Natl. Acad. Sci. USA, 1992, 89:10114-10118) Amplification and quantitation of the number of telomeric repeats according to the method of this disclosure is useful for determining disease risk or prognosis and taking appropriate interventional steps as described above.

In one aspect of the present disclosure, both the presence and the progress of telomeric-specific diseases may be determined using samples. Telomeric diseases are associated with an abnormal or premature shortening of telomeres, which can, for example, result from defects in telomerase activity. Telomerase is a ribonucleoprotein complex required for the replication and protection of telomeric DNA in eukaryotes. Cells lacking telomerase undergo a progressive loss of telomeric DNA that results in loss of viability and a concomitant increase in genome instability. These diseases may be inherited and include certain forms of congenital aplastic anemia, in which insufficient cell divisions in the stem cells of the bone marrow lead to severe anemia. Certain inherited diseases of the skin and the lungs are also caused by telomerase defects. For telomere diseases, a threshold for $T/S<0.5$ is appropriate for some conditions. Also, a commonly used metric is an age-adjusted percentile telomere score less than <10% or preferably <1% relative to a normal population.

Dyskeratosis congenita (DKC), also known as Zinsser-Engman-Cole syndrome, is a rare, progressive bone marrow failure syndrome characterized by mucocutaneous abnormalities: reticulated skin hyperpigmentation, nail dystrophy, and oral leukoplakia (Jyonouchi S. et al., Pediatr. Allergy Immunol., 2011, 22(3):313-9; Bessler M., et al., Haematologica, 2007, 92(8):1009-12). Evidence exists for telomerase dysfunction, ribosome deficiency, and protein synthesis dysfunction in this disorder. Early mortality is often associated with bone marrow failure, infections, fatal pulmonary complications, or malignancy. The disease is inherited in one of three types: autosomal dominant, autosomal recessive, or the most common form, X-linked recessive (where the gene responsible for DC is carried on the X-chromosome). Early diagnosis and measurement of disease progress using the method of this disclosure is very beneficial for families with these genetic characteristics so that early treatment with anabolic steroids or bone-marrow-stimulating drugs can help prevent bone marrow failure. The non-invasive, patient friendly saliva-testing method of the present disclosure is particularly useful for DKC because babies and small children need testing and continued monitoring.

Idiopathic interstitial pneumonias are characterized by damage to the lung parenchyma by a combination of fibrosis and inflammation. Idiopathic pulmonary fibrosis (IPF) is an example of these diseases that causes progressive scarring of the lungs. Fibrous scar tissue builds up in the lungs over time, affecting their ability to provide the body with enough oxygen. Heterozygous mutations in the coding regions of the telomerase genes, TERT and TERC, have been found in familial and sporadic cases of idiopathic interstitial pneumonia. All affected patients with mutations have short telomeres. A significant fraction of individuals with IPF have short telomere lengths that cannot be explained by coding mutations in telomerase (Cronkhite, J. T., et al., Am. J. Resp. Crit. Care Med., 2008, 178:729-737). Thus, telomere shortening can be used as a marker for an increased predisposition toward this age-associated disease (Alder, J. K., et al., Proc. Natl. Acad. Sci. USA, 2008, 105(35):13051-13056). Further, the course of IPF varies from person to person. For some, the disease may progress slowly and gradually over years, while for others it may progress rapidly. The method of the present may be conveniently used to monitor the course of pulmonary fibrosis and taking appropriate interventional steps as described above.

Aplastic anemia is a disease in which bone marrow stops making enough red blood cells, white blood cells and platelets for the body. Any blood cells that the marrow does make are normal, but there are not enough of them. Aplastic anemia can be moderate, severe or very severe. People with severe or very severe aplastic anemia are at risk for life-threatening infections or bleeding. Patients with aplastic anemia who have short telomeres, or are carrying telomerase mutations, have an increased risk of developing myelodysplasia and genomic instability leading to chromosomal aberrations and cancer (Calado et al. Leukemia (2011), 1-8).

Telomerase deficiency may cause variable degrees of telomere shortening in hematopoietic stem cells and lead to chromosomal instability and malignant transformation (Calado, R. T. and Young, N. S., The Hematologist, 2010 world wide web URL hematology.org/Publications/Hematologist/2010/4849.aspx). Aplastic anemia patients with shorter telomeres have a lower survival rate and are much more likely to relapse after immunotherapy than those with longer telomeres. Scheinberg et al. (JAMA, 2010, 304(12):1358-1364) found that relapse rates dropped as telomere lengths increased. The group of patients with the shortest telomeres was also at greater risk for a conversion to bone marrow cancer and had the lowest overall survival rates. The method of the present disclosure can be used in aplastic anemia patients to monitor the risk of developing major complications so that the clinical management of an individual may be tailored accordingly.

In another aspect, the present disclosure is useful in monitoring effectiveness of therapeutics or in screening for drug candidates affecting telomere length or telomerase activity. The ability to monitor telomere characteristics can provide a window for examining the effectiveness of particular therapies and pharmacological agents. The drug responsiveness of a disease state to a particular therapy in an individual can be determined by the method of the present disclosure. For example, the present disclosure finds use in monitoring the effectiveness of cancer therapy since the proliferative potential of cells is related to the maintenance of telomere integrity. As described above, while normal human somatic cells do not or only transiently express telomerase and therefore shorten their telomeres with each cell division, most human cancer cells typically express high levels of telomerase and show unlimited cell proliferation. Roth et al., (Small Molecules in Oncology, Recent Results in Cancer Research, U. M. Martens (ed.), Springer Verlag, 2010, pp. 221-234) have suggested that individuals with cancer who have very short telomeres in their tumors (in which the shortest telomeres in most cells are near to telomere dysfunction) and high telomerase activity might benefit the most from anti-cancer telomerase-inhibiting drugs. Because telomerase is either not expressed or expressed transiently and at very low levels in most normal cells, telomerase inhibition therapies may be less toxic to normal cells than conventional chemotherapy. An example of such drugs is the short oligonucleotide-based telomerase inhibitor imetelstat (previously named GRN163L). Imetelstat is a novel lipid-based conjugate of the first-generation oligonucleotide GRN163 (Asai, A. et al., Cancer Res., 2003, 63:3931-3939). However, cancer patients having very short telomeres in normal blood cells (particularly their granulocytes) are at higher risk of adverse effects of imetelstat on proliferative tissues such as the bone marrow. Rattain et al. (2008) found that such subjects with short granulocyte telomere length were more likely to have bone marrow failure symptoms such as neutropenia or thrombocytopenia. In this situation, a doctor might prescribe a lower dose of imetelstat, a different drug, or more frequent monitoring for bone marrow problems.

In other aspects, drug efficacy in the treatment of diseases of aging, for example but not limited to, cardiovascular disease, diabetes, pulmonary fibrosis, liver fibrosis, interstitial pneumonia and depression. In the case of cardiovascular disease, Brouilette et al. reported that middle-aged men with shorter telomere lengths than control groups benefit the most from lipid-lowering therapy with pravastatin (Brouilette, S. W. et al., Lancet, 2007, 369:107-114). Satoh et al. (Clin. Sci., 2009, 116:827-835) indicating that intensive lipid-lowering therapy protected telomeres from erosion better in patients treated with atorvastatin when compared with patients treated with moderate pravastatin therapy. The method of the present disclosure can be used to monitor the efficacy of statins in treated patients, wherein shorter telomere length correlates with better drug efficacy. Since subjects with the longest telomeres did not on average benefit from prophylactic statins, a doctor might suggest that the patient be especially compliant with good lifestyle habits as part of their treatment program. Conversely, patients with short telomeres who fear side effects of chronic statin usage might be persuaded to take statins based on their higher probability of benefiting from statins. Examples of statins that can be used include niacin (ADVICOR®, SIMCOR®), lovastatin (ALTOPREV®, MEVACOR®), amolopidine (CADUET®), rosuvastatin (CRESTOR®), sitagliptin/simvastatin (JUVISYNC®), fluvastatin (LESCOL®), pravastatin (PRAVACHOL®), atorvastatin (LIPITOR®), pitavastatin (LIVALO®), and ezetimibe/simvastatin (VYTORIN®).

Average telomere length per chromosome end determined from genomic DNA is a measure of overall telomere abundance, and this has been shown to correlate with several important biological indices. These indices include, for example, risk of various disease conditions, e.g., cardiovascular risk, cancer risk, pulmonary fibrosis risk, infectious disease risk, and risk of mortality. Abundance of telomeres also correlates with chronological age, body-mass index, hip/weight ratio, and perceived stress. One measurement of the average telomere length or abundance is the telomere/single copy ("T/S") ratio.

In a population, telomere length generally decreases with age. Accordingly, measures of average telomere length or abundance for an individual can be compared with measures for persons in the same age range in the population, that is, an age-matched population. For example, a person at age 30 might have a measure of telomere abundance about equal to the population average for age 30, or equal to the population average for age 20 or age 40. Correlations of a measure of average telomere length or abundance with measures of health can be more useful when compared with the measure for an age and gender-matched population. The range for an age matched population can be, for example, one year, two years, three years, four years, 5 years, 7 years or 10 years or up to 80 or more years.

Altered average telomere length or abundance or telomere length constitution determined from subject samples by the method of the present disclosure can be correlated with measures of health. Of particular interest are measures of health involving perceived stress. Apparent telomere shortening can be accelerated by genetic and environmental factors, including multiple forms of stress such as oxidative damage, biochemical stressors, chronic inflammation and viral infections (Epel, E. S. et al., Proc. Natl. Acad. Sci. USA, 2004, 49:17312-15). A convenient measure of general health status is the SF-36® Health Survey developed by John Ware (see, e.g., world wide web URL sf-36.org/tools/SF36.shtml). The SF-36 is a multi-purpose, short-form health survey with only 36 questions to be posed to patients, preferably by trained individuals. It provides an 8-scale profile of functional health and well-being scores as well as psychometrically-based physical and mental health summary measures and a preference-based health utility index. The SF-36 survey is used to estimate disease burden and compare disease-specific benchmarks with general population norms. The most frequently studied diseases and conditions include arthritis, back pain, cancer, cardiovascular disease, chronic obstructive pulmonary disease, depression, diabetes, gastro-intestinal disease, migraine headache, HIV/AIDS, hypertension, irritable bowel syndrome, kidney disease, low back pain, multiple sclerosis, musculoskeletal conditions, neuromuscular conditions, osteoarthritis, psychiatric diagnoses, rheumatoid arthritis, sleep disorders, spinal injuries, stroke, substance abuse, surgical procedures, transplantation and trauma (Turner-Bowker et al., SF-36® Health Survey & "SF" Bibliography: Third Edition (1988-2000), QualityMetric Incorporated, Lincoln, R. I., 2002). One skilled in the art will appreciate that other survey methods of general health status, for example, the RAND-36, may find use in the present disclosure.

In further aspects, drug effectiveness in the treatment of telomere-related conditions or diseases, for example but not limited to, dyskeratosis congenita, pulmonary fibrosis, and aplastic anemia, may be measured. For example, dyskeratosis congenita and pulmonary fibrosis are both treated with high-dose steroids, which are well known to have numerous deleterious side effects. Use of the lowest possible steroid dose is thus highly desirable, making the method of the present disclosure a valuable tool for monitoring these patients.

In another aspect, the present disclosure finds use as a general method of screening for candidate drugs, dietary supplements, and other interventions including lifestyle changes which affect biological pathways regulating telomere length, such as telomerase activity. Ability to rapidly and specifically amplify telomere repeats in a quantitative manner provides a high throughput screening method for identifying small molecules, candidate nucleic acids, and peptides agents and other products or interventions affecting telomere dynamics in a cell. Drug or other product candidates that have a positive, telomere lengthening effect on normal cells would be preferred in the treatment of degenerative, or cell senescence related conditions over those with telomere shortening (or telomerase inhibiting) effects, everything else being equal. In the case of treatment of cancer, drugs that have a negative, telomere shortening effect, especially in cancer cells would be preferred.

As used herein, the term "tumor" means a cancer or cancerous growth of any tissue or organ. Tumors include, without limitation, leukemias, lymphomas, and primary and metastatic cancers involving any one or more of bladder, bone, brain, breast, colon, esophagus, gall bladder, head and neck, kidney, liver, lung, meninges, muscle, ovary, pancreas, prostate, rectum, skin, small intestine, stomach, thyroid, ureter, and uterus.

The principle of telomere DNA-FISH is similar to that of telomere metaphase-FISH, with the exception that DNA is used as the test material. In an embodiment, the method in general includes 5 major steps.

Step 1: Purified genomic DNA is mixed with DNA binding/printing buffer and spotted onto glass surface of a standard glass slide or 96-well microplate with cover glass bottom;

Step 2: DNA samples in the microplate/slide are hybridized to a fluorescently labeled telomere probe, e.g., telomere peptide nucleic acid (PNA) probe, following a standard FISH procedure;

Step 3: The telomere fluorescent signals are detected by a fluorescent microscopy image system that is equipped with a digital camera, such as a charge-coupled device (CCD) or complementary metal oxide semiconductor (CMOS) camera;

Step 4: The digitized images are analyzed using a software that has spot counting and fluorescence intensity detection capability, such as those currently used by interphase qFISH (e.g., Telometer within ImageJ, Isis from MetaSystems Group, Inc., or METAMORPH® from Molecular Devices, LLC);

Step 5: Generate a standard curve using data from telomere length standards (e.g., 200 bp, 600 bp, 2.4 kb, 4.8 kb, 6.0 kb and 9.0 kb) that are included in each slide/plate. A statistical model, e.g., linear regression model ($TL_{bp}=\alpha+\beta TL_{FIU}$), is used to convert fluorescence intensity unit (HU) into absolute telomere length in bp, based on the α (intercept) and β (slope) generated from the standard curve.

Figure 1B:
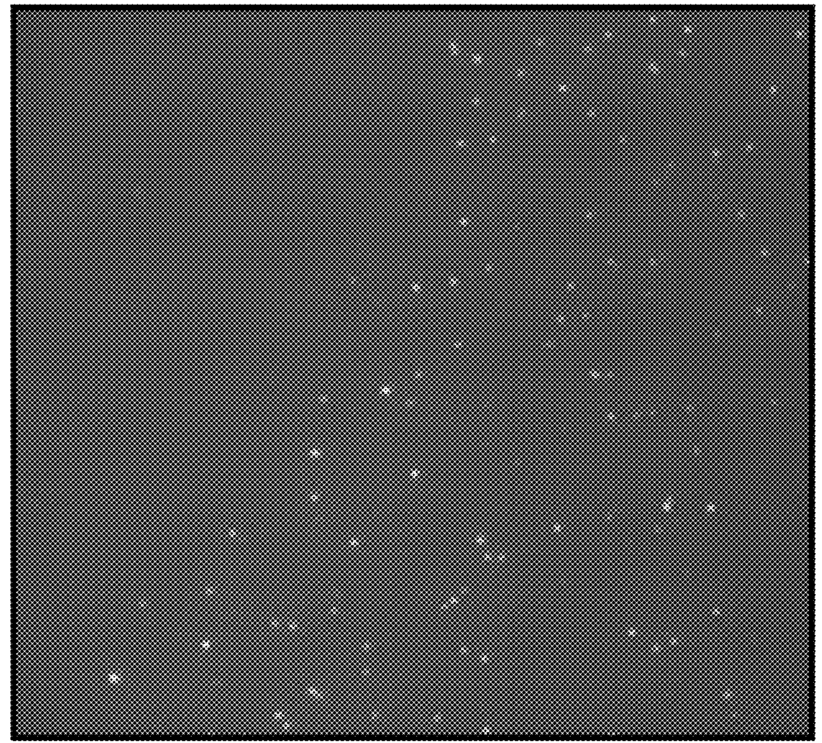
FIG. 1B is a photographic image depicting DNA-FISH of human genomic DNA purified from blood leukocytes. Shown is red telomere fluorescent signals of the same region as depicted in FIG. 1A. Image was obtained under a 100× oil objective. Each dot represents one telomere. Note the various intensities.
Figure 3A:
FIG. 3A is a photographic image depicting cloned telomere standards (0.2 kb) after DNA-FISH. Image was obtained under a 100× oil objective. Each dot represents one telomere fragment.
Figure 3B:
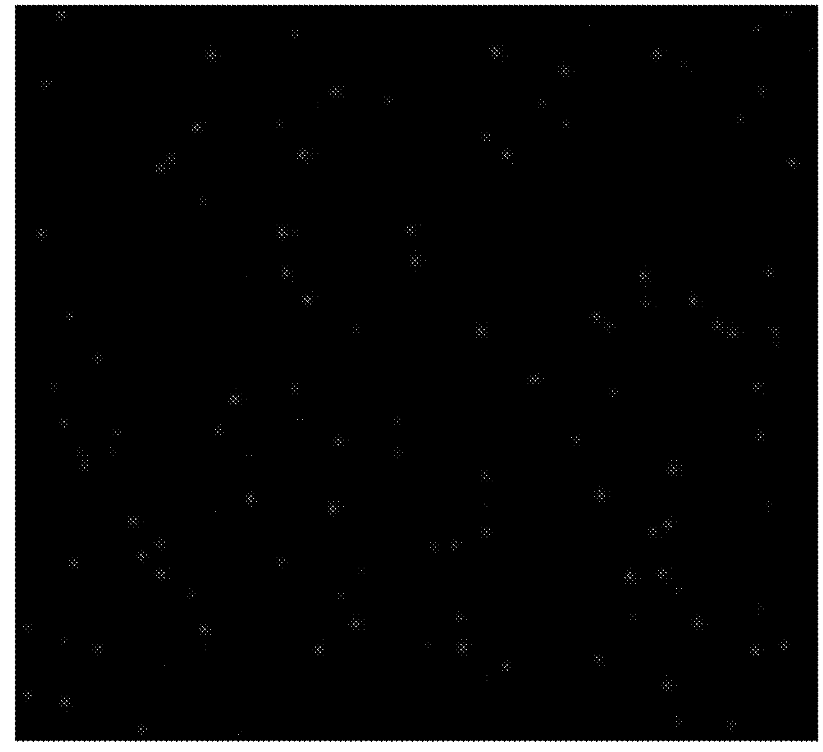
FIG. 3B is a photographic image depicting cloned telomere standards (0.9 kb) after DNA-FISH. Image was obtained under a 100× oil objective. Each dot represents one telomere fragment.

As described in greater detail below, results have shown that a typical image under a 100× objective contains approximately 150-300 telomeres (FIGS. 1B and 3). Thus, for each sample, 10 to 20 images can be analyzed to obtain TL measurement for approximately 3000 telomeres.

An aspect of the present disclosure is a method for determining telomere length, comprising:

a) immobilizing onto a substrate at least one sample of genomic DNA and a plurality of telomere length standards of different lengths;

b) contacting the immobilized genomic DNA and telomere length standards of step a) with a fluorescently labeled probe having a sequence complimentary to a telomere sequence under conditions such that said probe hybridizes specifically to telomeric DNA;

c) detecting hybridized probe with a fluorescent microscopy image system, thereby generating digitized images of the hybridized probe;

d) analyzing the digitized images for spot count and individual spot intensity;

e) generating a standard curve of telomere length in base-pair versus spot intensities based on the plurality of telomere length standards on the substrate;

f) determining at least one of the following for each sample of genomic DNA:

(i) average telomere length per telomere;
(ii) telomere length variation (TLV);
(iii) frequency of short telomeres; and
(iv) frequency of long telomeres.

In certain embodiments, the genomic DNA is human genomic DNA.

In certain embodiments, the telomere length standards are cloned telomere fragments. A method for making cloned telomere standards has been described in Beh, C. W et al. (2018) Nucleic Acids Res., 46(19) e117. A method for making cloned telomere standards is also described in Example 7 herein.

In certain embodiments, the plurality of telomere length standards of different lengths comprises telomere fragments of about 0.1 to about 2.4 kb. For example, telomere length standards can include telomere fragments of about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, or 2.4 kb. In certain embodiments, the plurality of telomere length standards of different lengths comprises telomere fragments of greater than about 2.4 kb. For example, telomere length standards can include telomere fragments of about 3.0, 4.0, 5.0, 6.0, 7.0, 8.0, 9.0, or 10.0 kb, and any length there between or above.

In certain embodiments, the substrate comprises a glass surface. For example, in an embodiment the substrate is a glass sheet or a glass microscope slide.

In certain embodiments, the substrate consists of glass. For example, in an embodiment the substrate is a glass sheet or a 96-well plate with cover glass bottom.

The image system usually has the following basic components: a fluorescent microscope, an automated stage, a digital camera, and a computer with specialized software that controls the stage and camera for automated image acquisition. In certain embodiments, the fluorescent microscopy image system comprises a digital camera, such as a charge-coupled device (CCD) or complementary metal oxide semiconductor (CMOS) camera.

In certain embodiments, step f) comprises determining each of the following for each sample of genomic DNA:

(i) average telomere length per telomere; and
(ii) telomere length variation.

In certain embodiments, step f) comprises determining each of the following for each sample of genomic DNA:

(i) average telomere length per telomere; and
(iii) frequency of short telomeres.

In certain embodiments, step f) comprises determining each of the following for each sample of genomic DNA:

(i) average telomere length per telomere; and
(iv) frequency of long telomeres.

In certain embodiments, step f) comprises determining each of the following for each sample of genomic DNA:

(ii) telomere length variation; and
(iii) frequency of short telomeres.

In certain embodiments, step f) comprises determining each of the following for each sample of genomic DNA:

(ii) telomere length variation; and
(iv) frequency of long telomeres.

In certain embodiments, step f) comprises determining each of the following for each sample of genomic DNA:

(iii) frequency of short telomeres; and
(iv) frequency of long telomeres.

In certain embodiments, step f) comprises determining each of the following for each sample of genomic DNA:

(i) average telomere length per telomere;
(ii) telomere length variation; and
(iii) frequency of short telomeres.

In certain embodiments, step f) comprises determining each of the following for each sample of genomic DNA:

(i) average telomere length per telomere;
(ii) telomere length variation; and
(iv) frequency of long telomeres.

In certain embodiments, step f) comprises determining each of the following for each sample of genomic DNA:

(i) average telomere length per telomere;
(iii) frequency of short telomeres; and
(iv) frequency of long telomeres.

In certain embodiments, step f) comprises determining each of the following for each sample of genomic DNA:

(ii) telomere length variation;
(iii) frequency of short telomeres; and
(iv) frequency of long telomeres.

In certain embodiments, step f) comprises determining each of the following for each sample of genomic DNA:

(i) average telomere length per telomere;
(ii) telomere length variation;
(iii) frequency of short telomeres; and
(iv) frequency of long telomeres.

In certain embodiments, the short telomeres are less than or equal to about 4 kb long. For example, in certain embodiments, the short telomeres are less than or equal to about 1.0, 2.0, 3.0, or 4.0 kb long.

In certain embodiments, the short telomeres are less than or equal to about 1 kb long. For example, in certain embodiments, the short telomeres are less than or equal to about 0.5, 0.6, 0.7, 0.8, 0.9, or 1.0 kb long.

In certain embodiments, the long telomeres are greater than or equal to about 11 kb long. For example, in certain embodiments, the long telomeres are greater than or equal to about 11, 12, 13, 14, 15, 16, 17, 18, 19, or 20 kb long. In certain embodiments, the long telomeres are about 11, 12, 13, 14, 15, 16, 17, 18, 19, or 20 kb long. In certain embodiments, the long telomeres are greater than or equal to about 30, 40, 50, 60, 70, 80, 90, 100, or 200 kb long. In certain embodiments, the long telomeres are about 30, 40, 50, 60, 70, 80, 90, 100, or 200 kb long.

In certain embodiments, the long telomeres are greater than or equal to about 15 kb long.

In certain embodiments, at least about 1000 telomeres are analyzed for each sample of genomic DNA. In certain embodiments, at least about 2000 telomeres are analyzed for each sample of genomic DNA. In certain embodiments, at least about 3000 telomeres are analyzed for each sample of genomic DNA.

In certain embodiments, about 3000 telomeres are analyzed for each sample of genomic DNA.

In certain embodiments, the at least one sample of genomic DNA comprises DNA isolated from one or more tissue obtained from a subject, wherein the tissue is selected from the group consisting of blood, bone marrow, skin, bone, muscle, heart, blood vessel, lung, prostate, breast, colon, rectum, kidney, bladder, lymph node, thyroid, uterus, ovary, brain, tongue, mouth, esophagus, stomach, liver, spleen, pancreas, small intestine, and cervix.

In certain embodiments, the at least one sample of genomic DNA comprises DNA isolated from one or more cell type obtained from a subject, wherein the cell type is selected from the group consisting of buffy coat, peripheral blood mononuclear cells (PBMCs), lymphocytes, monocytes, granulocytes, and any combination thereof.

In certain embodiments, the at least one sample of genomic DNA comprises DNA isolated from buffy coat.

In certain embodiments, the at least one sample of genomic DNA comprises DNA isolated from PBMCs.

In certain embodiments, the at least one sample of genomic DNA comprises DNA isolated from lymphocytes.

In certain embodiments, the at least one sample of genomic DNA comprises DNA isolated from monocytes.

In certain embodiments, the at least one sample of genomic DNA comprises DNA isolated from granulocytes.

In certain embodiments, the at least one sample of genomic DNA comprises DNA isolated from a tumor obtained from a subject.

In certain embodiments, the at least one sample of genomic DNA comprises DNA isolated from one or more cell type obtained from a subject, wherein the cell type is selected from the group consisting of circulating tumor cells, circulating stem cells, and any combination thereof.

In certain embodiments, the at least one sample of genomic DNA comprises DNA isolated from circulating tumor cells.

In certain embodiments, the at least one sample of genomic DNA comprises DNA isolated from circulating stem cells.

In certain embodiments, the at least one sample of genomic DNA comprises DNA isolated from circulating cancer stem cells.

An aspect of the present disclosure is a substrate comprising a surface onto which a plurality of telomere length standards of different lengths is immobilized.

In certain embodiments, the telomere length standards are cloned telomere fragments.

In certain embodiments, the telomere length standards are telomere DNA purified from cells with known telomere length.

In certain embodiments, the plurality of telomere length standards of different lengths comprises telomere fragments of about 0.1 to about 2.4 kb.

In certain embodiments, the substrate further comprises at least one sample of genomic DNA immobilized onto the surface.

In certain embodiments, the at least one sample of genomic DNA comprises DNA isolated from one or more tissue obtained from a subject, wherein the tissue is selected from the group consisting of blood, bone marrow, skin, bone, muscle, heart, blood vessel, lung, prostate, breast, colon, rectum, kidney, bladder, lymph node, thyroid, uterus, ovary, brain, tongue, mouth, esophagus, stomach, liver, spleen, pancreas, small intestine, and cervix.

In certain embodiments, the at least one sample of genomic DNA comprises DNA isolated from one or more cell type obtained from a subject, wherein the cell type is selected from the group consisting of buffy coat, peripheral blood mononuclear cells (PBMCs), lymphocytes, monocytes, granulocytes, and any combination thereof.

In certain embodiments, the at least one sample of genomic DNA comprises DNA isolated from a tumor obtained from a subject.

In certain embodiments, the at least one sample of genomic DNA comprises DNA isolated from one or more cell type obtained from a subject, wherein the cell type is selected from the group consisting of circulating tumor cells, circulating stem cells, and any combination thereof.

An aspect of the present disclosure is a kit, comprising a plurality of telomere length standards of different lengths.

In certain embodiments, the telomere length standards are cloned telomere standards.

In certain embodiments, the plurality of telomere length standards of different lengths comprises telomere lengths of about 0.1 to about 9.0 kb. For example, in certain embodiments, the plurality of telomere length standards of different lengths comprises telomere lengths of about 0.1 to about 2.0, 2.4, 3.0, 4.0, 5.0, 6.0, 7.0, 8.0, or 9.0 kb.

In certain embodiments, the kit further comprises a DNA binding buffer (e.g., a sodium iodide solution) or a DNA printing buffer (e.g., a 1.5 M Betaine, 0.45 M sodium chloride and 0.045 M sodium citrate solution).

In certain embodiments, the kit further comprises a hybridization buffer.

In certain embodiments, the kit further comprises a DNA binding buffer and a hybridization buffer.

In certain embodiments, the kit further comprises a DNA printing buffer and a hybridization buffer.

In certain embodiments, the kit comprises a plurality of telomere length standards of different lengths, a DNA printing/binding buffer, and a hybridization buffer.

In certain embodiments, the kit further comprises a fluorescently labeled probe having a sequence complimentary to a telomere sequence.

In certain embodiments, the kit comprises a plurality of telomere length standards of different lengths, a DNA printing/binding buffer, a hybridization buffer, and a fluorescently labeled probe having a sequence complimentary to a telomere sequence.

An aspect of the present disclosure is a method for diagnosing a telomere-related condition or disease in a subject, comprising:

a) obtaining a biological sample from a subject;

b) immobilizing onto a substrate at least one sample of genomic DNA derived from the biological sample and a plurality of telomere length standards of different lengths;

c) contacting the immobilized genomic DNA and plurality of telomere length standards of different lengths of step b) with a fluorescently labeled probe having a sequence complimentary to a telomere sequence under conditions such that said probe hybridizes specifically to telomeric DNA;

d) detecting hybridized probe with a fluorescent microscopy image system, thereby generating digitized images of the hybridized probe;

e) analyzing the digitized images for spot count and individual spot intensity;

f) generating a standard curve of telomere length versus spot intensities based on the plurality of telomere length standards on the substrate;

g) determining at least one of the following for each sample of genomic DNA:

(i) average telomere length per telomere;

(ii) telomere length variation (TLV);

(iii) frequency of short telomeres; and (iv) frequency of long telomeres; and h) diagnosing the subject as having the telomere-related condition or disease based on the information obtained in step g).

In certain embodiments, the telomere-related condition or disease is selected from the group consisting of aging, certain congenital syndromes, cancer, cardiovascular disease, diabetes mellitus (viz., type 1 diabetes and type 2 diabetes), cirrhosis, infection with human immunodeficiency virus (HIV), Hutchinson Gilford progeria, dyskeratosis congenita, idiopathic pulmonary fibrosis, and aplastic anemia. In certain embodiments, the telomere-related condition or disease is selected from the group consisting of dyskeratosis congenita, pulmonary fibrosis, and aplastic anemia. In certain embodiments, the telomere-related condition or disease is aging. In certain embodiments, the telomere-related condition or disease is cancer. In certain embodiments, the telomere-related condition or disease is cardiovascular disease. In certain embodiments, the telomere-related condition or disease is type 1 diabetes mellitus. In certain embodiments, the telomere-related condition or disease is type 2 diabetes mellitus. In certain embodiments, the telomere-related condition or disease is hepatic cirrhosis. In certain embodiments, the telomere-related condition or disease is progeria. In certain embodiments, the telomere-related condition or disease is dyskeratosis congenita. In certain embodiments, the telomere-related condition or disease is pulmonary fibrosis, including idiopathic pulmonary fibrosis. In certain embodiments, the telomere-related condition or disease is aplastic anemia.

An aspect of the present disclosure is a method for assessing general health and/or aging of a subject, comprising:

a) obtaining a biological sample from a subject;

b) immobilizing onto a substrate at least one sample of genomic DNA derived from the biological sample and a plurality of telomere length standards of different lengths;

c) contacting the immobilized genomic DNA and plurality of telomere length standards of different lengths of step b) with a fluorescently labeled probe having a sequence complimentary to a telomere sequence under conditions such that said probe hybridizes specifically to telomeric DNA;

d) detecting hybridized probe with a fluorescent microscopy image system, thereby generating digitized images of the hybridized probe;

e) analyzing the digitized images for spot count and individual spot intensity;

f) generating a standard curve of telomere length versus spot intensities based on the plurality of telomere length standards on the substrate;

g) determining at least one of the following for each sample of genomic DNA:

(i) average telomere length per telomere;

(ii) telomere length variation (TLV);

(iii) frequency of short telomeres; and (iv) frequency of long telomeres; and h) identifying the subject as having normal or abnormal general health and/or aging based on the information obtained in step g).

In some embodiments, the method is a method for assessing general health of a subject.

In some embodiments, the method is a method for assessing aging of a subject.

In some embodiments, the method is a method for assessing general health and aging of a subject.

For example, a subject may be said to have normal general health when the telomere length assessment is within a normal range for generally healthy individuals. Conversely, a subject may be said to have abnormal general health when the telomere length assessment is outside a normal range for generally healthy individuals, e.g., telomeres are shorter on average, have increased TLV, and/or the frequency of short telomeres or long telomeres is higher than the normal range for generally healthy individuals.

Similarly, a subject may be said to have normal aging when the telomere length assessment is within a normal range for individuals of the same or similar age as the subject. Conversely, a subject may be said to have abnormal aging when the telomere length assessment is outside a normal range for individuals of the same or similar age as the subject, e.g., telomeres are shorter on average, have increased TLV, and/or the frequency of short telomeres or long telomeres is higher than the normal range for individuals of the same or similar age as the individual. The expression "same age" can mean, for example, about 60 years, about 61 years, about 62 years, about 63 years, about 64 years, about 65 years, about 66 years, about 67 years, about 68 years, about 69 years, about 70 years, etc. The expression "similar age" can mean, for example, the same decade of age (e.g., 60s, 70s, 80s, 90s) or within a certain range of years of age around the age of the subject, e.g., 60±5 years, 65±5 years, 70±5 years, etc. The range can be broadened or narrowed, for example 60±1 year, 60±2 years, 60±3 years, 60±4 years, 60±6 years, 60±7 years, 60±8 years, 60±9 years, 60±10 years, etc.

An aspect of the present disclosure is a method for establishing a relationship between telomere constitution and cancer and/or aging-related disease, comprising:

a) obtaining a biological sample from each of a population of subjects;

b) immobilizing onto a substrate at least one sample of genomic DNA derived from the biological sample and a plurality of telomere length standards of different lengths;

c) contacting the immobilized genomic DNA and plurality of telomere length standards of different lengths of step b) with a fluorescently labeled probe having a sequence complimentary to a telomere sequence under conditions such that said probe hybridizes specifically to telomeric DNA;

d) detecting hybridized probe with a fluorescent microscopy image system, thereby generating digitized images of the hybridized probe;

e) analyzing the digitized images for spot count and individual spot intensity;

f) generating a standard curve of telomere length versus spot intensities based on the plurality of telomere length standards on the substrate;

g) determining at least one of the following for each sample of genomic DNA:
   (i) average telomere length per telomere;
   (ii) telomere length variation (TLV);
   (iii) frequency of short telomeres; and
   (iv) frequency of long telomeres; and
h) identifying a relationship between telomere constitution and cancer and/or aging-related disease based on the information obtained in step g).

A relationship between telomere constitution and cancer and/or aging-related disease can be said to be present when average telomere length, TLV, frequency of short telomeres, and/or frequency of long telomeres are substantially similar in or characteristic of a population of subjects having cancer and/or aging-related disease. Conversely, a relationship between telomere constitution and cancer and/or aging-related disease can be said to be absent when average telomere length, TLV, frequency of short telomeres, and/or frequency of long telomeres are substantially dissimilar in or uncharacteristic of a population of subjects having cancer and/or aging-related disease.

In some embodiments, the method is a method for establishing a relationship between telomere constitution and cancer. The cancer can be of any type, including, without limitation, leukemias, lymphomas, and primary and metastatic cancers involving any one or more of bladder, bone, brain, breast, colon, esophagus, gall bladder, head and neck, kidney, liver, lung, meninges, muscle, ovary, pancreas, prostate, rectum, skin, small intestine, stomach, thyroid, ureter, and uterus.

In some embodiments, the method is a method for confirming a known or suspected relationship between telomere constitution and cancer. In some embodiments, the method is a method for confirming a known relationship between telomere constitution and cancer. In some embodiments, the method is a method for confirming a suspected relationship between telomere constitution and cancer.

In some embodiments, the method is a method for studying a known or suspected relationship between telomere constitution and cancer. In some embodiments, the method is a method for studying a known relationship between telomere constitution and cancer. In some embodiments, the method is a method for studying a suspected relationship between telomere constitution and cancer.

In some embodiments, the method is a method for establishing a relationship between telomere constitution and aging-related disease. The aging-related disease can be of any type, including, without limitation, cardiovascular disease, diabetes, pulmonary fibrosis, liver fibrosis, interstitial pneumonia, and depression.

In some embodiments, the method is a method for confirming a known or suspected relationship between telomere constitution and aging-related disease. In some embodiments, the method is a method for confirming a known relationship between telomere constitution and aging-related disease. In some embodiments, the method is a method for confirming a suspected relationship between telomere constitution and aging-related disease.

In some embodiments, the method is a method for studying a known or suspected relationship between telomere constitution and aging-related disease. In some embodiments, the method is a method for studying a known relationship between telomere constitution and aging-related disease. In some embodiments, the method is a method for studying a suspected relationship between telomere constitution and aging-related disease.

An aspect of the present disclosure is a method for assessing exposure to harmful substances and/or stresses of a subject, comprising:
a) obtaining a biological sample from a subject;
b) immobilizing onto a substrate at least one sample of genomic DNA derived from the biological sample and a plurality of telomere length standards of different lengths;
c) contacting the immobilized genomic DNA and plurality of telomere length standards of different lengths of step b) with a fluorescently labeled probe having a sequence complimentary to a telomere sequence under conditions such that said probe hybridizes specifically to telomeric DNA;
d) detecting hybridized probe with a fluorescent microscopy image system, thereby generating digitized images of the hybridized probe;
e) analyzing the digitized images for spot count and individual spot fluorescent intensity;
f) generating a standard curve of telomere length in base-pair versus spot fluorescent intensities based on the plurality of telomere length standards on the substrate;
g) determining at least one of the following for each sample of genomic DNA:
   (i) average telomere length per telomere;
   (ii) telomere length variation (TLV);
   (iii) frequency of short telomeres; and
   (iv) frequency of long telomeres; and
h) identifying the subject as having harmful exposure or not based on the information obtained in step g).

An aspect of the invention is a method for assessing response to a drug or drugs treatment of a subject, comprising:
a) obtaining a biological sample from a subject;
b) immobilizing onto a substrate at least one sample of genomic DNA derived from the biological sample and a plurality of telomere length standards of different lengths;
c) contacting the immobilized genomic DNA and plurality of telomere length standards of different lengths of step b) with a fluorescently labeled probe having a sequence complimentary to a telomere sequence under conditions such that said probe hybridizes specifically to telomeric DNA;
d) detecting hybridized probe with a fluorescent microscopy image system, thereby generating digitized images of the hybridized probe;
e) analyzing the digitized images for spot count and individual spot fluorescent intensity;
f) generating a standard curve of telomere length in base-pair versus spot fluorescent intensities based on the plurality of telomere length standards on the substrate;
g) determining at least one of the following for each sample of genomic DNA:
   (i) average telomere length per telomere;
   (ii) telomere length variation (TLV);
   (iii) frequency of short telomeres; and
   (iv) frequency of long telomeres; and
h) determining the effect of the drug/drugs on the subject based on the information obtained in step g).

An aspect of the invention is a method for assessing disease risk of a subject, comprising:

a) obtaining a biological sample from a subject;

b) immobilizing onto a substrate at least one sample of genomic DNA derived from the biological sample and a plurality of telomere length standards of different lengths;

c) contacting the immobilized genomic DNA and plurality of telomere length standards of different lengths of step b) with a fluorescently labeled probe having a sequence complimentary to a telomere sequence under conditions such that said probe hybridizes specifically to telomeric DNA;

d) detecting hybridized probe with a fluorescent microscopy image system, thereby generating digitized images of the hybridized probe;

e) analyzing the digitized images for spot count and individual spot fluorescent intensity;

f) generating a standard curve of telomere length in base-pair versus spot fluorescent intensities based on the plurality of telomere length standards on the substrate;

g) determining at least one of the following for each sample of genomic DNA:

(i) average telomere length per telomere;

(ii) telomere length variation (TLV);

(iii) frequency of short telomeres; and (iv) frequency of long telomeres; and h) determining the subject's risk category for a disease/diseases based on the information obtained in step g).

An aspect of the invention is a method for assessing clinical outcome of a subject who is suffering from a disease/diseases, comprising:

a) obtaining a biological sample from a subject;

b) immobilizing onto a substrate at least one sample of genomic DNA derived from the biological sample and a plurality of telomere length standards of different lengths;

c) contacting the immobilized genomic DNA and plurality of telomere length standards of different lengths of step b) with a fluorescently labeled probe having a sequence complimentary to a telomere sequence under conditions such that said probe hybridizes specifically to telomeric DNA;

d) detecting hybridized probe with a fluorescent microscopy image system, thereby generating digitized images of the hybridized probe;

e) analyzing the digitized images for spot count and individual spot fluorescent intensity;

f) generating a standard curve of telomere length in base-pair versus spot fluorescent intensities based on the plurality of telomere length standards on the substrate;

g) determining at least one of the following for each sample of genomic DNA:

(i) average telomere length per telomere;

(ii) telomere length variation (TLV);

(iii) frequency of short telomeres; and (iv) frequency of long telomeres; and h) determining the likelihood of survival/recovery from the disease/diseases of the subject based on the information obtained in step g).

EXAMPLES

Example 1. Biological Sample Collection and Storage

For large population studies, biological sample collections predominantly involve peripheral blood and oral cells (collected by mouthwash or buccal swabs). Peripheral whole blood can be processed to yield buffy coat, PBMCs and granulocytes which are the starting material for purification of genomic DNA. Generally it is preferable to process blood sample with 24 hours of collection. Processed sample aliquots should be stored at −80° C. until the TL assay is performed. EDTA is the usual anticoagulant used to collect blood for DNA analysis. DNA extracted from dried blood spots (DBS) collected on Whatman cards from finger or heel sticks has been used for Q-PCR TL measurement and has been reported to have a high correlation with venous blood. However, T/S ratios measured from DBS is higher than that from venous blood and the inter-assay CV is also higher. DBS has the advantage of being cost efficient, but is not the optimal method to collect blood samples for TL measurement. If archived DBS samples will be used for TL measurement, the method may further include examining the integrity of DNA by gel electrophoresis An increasing number of studies have used DNA extracted from oral cells for TL measurement. Several methods have been used to collect oral cells, including passive drooling, mouthwashes, saliva swabs, and buccal swabs/brushes. These alternative collection methods allow home collection and offer the possibility of collecting biological material when blood draw is not practical. However, caution is warranted when oral cells are used for TL measurement. Oral cells contain mixture of buccal cells, white blood cells, and bacteria, and the percentage of buccal cells varies significantly between collection methods. Generally it is preferable to use buccal swabs to collect buccal cells for TL measurement because buccal swabs collect predominantly buccal epithelial cells with rare blood white cell contamination. Commercially available buccal swabs that are specifically designed to collect buccal cells for DNA testing offer advantages including standardized collection methods and sample stability at room temperature for long periods of time (3 years).

Example 2. Cell Type/Tissue Type Consideration

Average telomere lengths from different cell/tissue types from the same individuals have been reported to differ substantially. The TL differences between different tissue/cell types are considerably larger than the group differences found using a single tissue/cell source in most studies. Thus generally it is preferred to use one tissue/cell type for a specific study, and combining data from different tissue/cell types is not advisable. A more complicated issue to address is that each tissue source contains variable number of different cell types. The ratio of different cell types can vary within a single tissue source at different time points of collection, indicating that careful consideration of the relative length of telomeres by cell type is needed when designing studies. For example, blood leukocytes (buffy coat) is the most commonly used material for TL measurement by Q-PCR, and leukocytes include T lymphocytes, B lymphocytes, monocytes, granulocytes, etc. Previous studies have consistently demonstrated that average TL differed significantly between these cell types, with B lymphocytes having longer TL than T lymphocytes and naïve cells have longer TL than memory cells. Therefore, interpretations of TL differences should consider the possibility that the differences may due to variations in cell compositions.

Most of the published large population studies used blood leukocytes for TL measurement. It is important to consider the dynamic nature of immune system in response to recent infections and illness. We recommend developing guidelines on inclusion/exclusion criteria for collecting blood for TL measurement. Studies should avoid collecting blood samples if participants are showing sign of infection, have recently had a major surgery or injury, are taking immunosuppressive drugs, or have recently had chemotherapy or radiation therapy. It is desirable to measure TL in specific cell types that are purified either by cell sorting or by magnetic cell separation, but this is often impractical for archived samples and for large population studies. When DNA from buffy coat (leukocytes) is used for TL measurement, we recommend performing a simple blood white cell composition count to be used as a covariate in data analysis step.

At present there are significant knowledge gaps regarding the optimal cell type to use for studying the associations between TL and diseases or environmental exposures. To fill these knowledge gaps, large population studies are needed to collect and store purified blood cells (i.e., $CD4^+$ T lymphocytes, $CD8^+$ and $CD28^-$ T lymphocytes, $CD19^+$ B lymphocytes, granulocytes etc.) and buccal cells. DNA purified from each of these different cell types for TL measurement can be correlated with diseases or environmental exposures.

We have archived blood products, including buffy coat, PBMCs, granulocytes, and cultured blood lymphocytes (metaphase chromosomes), from participants in a previous study (N=465). These blood samples were collected during 2005-2013 in a breast cancer case-control study (Zheng Y. L. et al. (2009) *Carcinogenesis,* 30, 1380-1386; Zheng, Y. L. et al. (2011) *Hum. Mol. Genet.,* 20, 378-386), and the processed blood products have been stored at −80° C. (buffy coat, PBMC, granulocytes) or −20° C. (metaphase chromosomes) for 5 to 13 years. All the blood samples were collected before surgery, chemotherapy, radiation therapy, and one month after subjects stopped taking immunosuppressive drugs or antibiotics. Questionnaire data, including demographics, tobacco use, alcohol drinking, physical activity and occupation, etc., are available. Detailed characteristics of the study population were described in Zheng et al. (2009) and (2011) (supra).

Several questions are addressed using this sample resource:

1) Do TLs differ between buffy coats, PBMCs, granulocytes or cultured lymphocytes?
2) Are strengths of association between cell-type specific TLs and breast cancer risk different?
3) Which cell-type specific TL is associated with environmental exposures, e.g., tobacco smoking, and life style factors, e.g., physical activity?

The results provide some insights on future sample collection and processing recommendations for epidemiological studies. Further, buffy coats, PBMCs, and granulocytes are readily obtainable across a broad range of population studies by adding a gradient centrifugation step during blood processing, which is feasible for large population studies.

Example 3. DNA Extraction

The general consensus is that high quality genomic DNA is required for TL measurement using Q-PCR. DNA samples that are degraded or impure have been shown to bias T/S ratio by Q-PCR. We recommend extracting all the DNA samples using the same method for a study. Based on our experience and those reported by others, membrane filter-based method, such as QIAmp DNA kit from Qiagen, is preferred over salt-out method. It is preferred to extract DNA in batches shortly before TL measurement for a study if possible. Otherwise, extracted DNA should be stored at −80° C. at high concentration (>25 ng/4) until TL measurement.

Example 4. Substrate for DNA-FISH

One of the key steps of the DNA-FISH method is to find an appropriate solid support for DNA immobilization. We searched techniques that were applied to DNA microarray applications and decided to use glass as solid support surface for our method because the intrinsic properties of glass, including low fluorescence, excellent flatness, chemical inertness, and low cost. The next important component of the method is immobilizing DNA on a glass surface. Coating with silane molecule has been shown to establish a functional surface to binds organic molecules such as DNA. However, surface preparation and organo-silane deposition technique must all be carefully controlled to achieve a smooth, even surface coating.

Example 5. DNA Printing Buffer

We optimized a DNA printing buffer that showed high binding affinity of DNA to an aminosilane-coated glass surface after FISH. This DNA printing buffer is an aqueous solution comprising 1.5 M betaine, 0.45 M sodium chloride and 0.045 M sodium citrate. High density DNA microarrays that were printed using this buffer showed even and homogenous spot morphology for downstream FISH analysis. After FISH, well-separated telomere signals were visualized and captured using an epifluorescence microscope equipped with a CCD camera under 100× oil objective. Digitized images were analyzed using ImageJ with a custom plugin (Telometer, developed by Dr. Alan Meeker's team at Johns Hopkins University) to quantify the fluorescent telomere signals.

Example 6. DNA Binding Buffer

We developed a DNA binding buffer that showed high binding affinity of DNA to a glass surface after FISH. This binding buffer is an aqueous solution comprising 6.6 M sodium iodide (NaI) and 16 mM sodium sulfite ($Na_2SO_3$). The DNA binding buffer also facilitated even DNA spreading on a glass surface. This is particularly important because well-separated telomeres are required for the digitized images to be analyzed automatically by spot counting software. After FISH, images were captured using an epifluorescence microscope equipped with a CCD camera under 100× oil objective. Digitized images were analyzed using ImageJ with a custom plugin (Telometer, developed by Dr. Alan Meeker's team at Johns Hopkins University) to quantify the fluorescent telomere signals.

Example 7. Molecular Cloning of Telomere Fragments as Telomere Standards for DNA-FISH Seven cloned telomere molecules of 0.1 kb, 0.2 kb, 0.4 kb, 0.6 kb, 0.9 kb, 1.2 kb, and 2.4 kb were obtained by molecular cloning of synthetic telomere repeats. All clones were confirmed by DNA sequencing. These short telomere clones have been used for developing and testing the sensitivity of the telomere DNA-FISH method. Further cloning will attempt to obtain clones containing larger telomere fragments, e.g., 4.8 kb, 8.0 kb, and 12 kb.

The cloning procedure uses synthetic telomere template $(TTAGGG)_{12}$ (SEQ ID NO: 1) containing KpnI and XhoI restriction enzyme sites at 5' end and SalI at 3' end that was cloned into a plasmid vector, pUC19. The telomere repeats in the vector were either released by restriction enzyme digestion (KpnI and SalI) or amplified by PCR using two pUC19 vector-specific primers outside the insert (pUC19-F: AGTGAATTCGAGCTCGGTAC (SEQ ID NO: 2) and pUC19-R: CAAGCTTGCATGCCTGCAG (SEQ ID NO: 3)) for the next round extension. A second vector containing the telomere repeats was cut open at XhoI site by restriction enzyme digestion to serve as a receiving vector. The receiving vector and telomere inserts were incubated with NEBuilder HiFi DNA assembling master mix from New England BioLabs (Ipswich, MA) to complete chewing back, annealing, and ligating steps in one reaction (99). The resulting telomere size was the sum of telomere insert plus the telomere repeats of the receiving vector. After transforming into *E. coli*, the vector containing the telomere repeats was enriched and purified as a telomere standard.

Example 8. Experimental Design

The method uses purified genomic DNA, thus is flexible for analyzing fresh and archived tissues/cells. If TL results from a specific cell type are desired, the cells are isolated either by cell sorting or magnetic cell separation prior to DNA purification. Because no enzymatic reaction is involved in DNA-FISH, the method works well with impure DNA samples, decreasing the assay variabilities that are caused by DNA extraction methods and sample collection and storage conditions. This is a significant advantage for population studies when samples are typically collected over a long time period and stored under diverse conditions. High molecular weight (non-degraded) DNA is required to make sure telomere molecules are intact. In degraded DNA, telomere repeats are lost or degraded, leading to falsely short TL results. In general, non-degraded DNA is required for DNA-based TL measurement, such as by TRF and by Q-PCR.

The method in general includes 5 major steps.

- Step 1: Purified genomic DNA is mixed with DNA printing or DNA binding buffer and spotted onto glass surface of a standard glass slide or a standard 96-well microplate with cover glass bottom.
- Step 2: DNA samples in the microplate/slide are hybridized to a fluorescently labeled telomere probe, e.g., telomere peptide nucleic acid (PNA) probe, following a standard FISH procedure.
- Step 3: The telomere fluorescent signals are detected by a fluorescent microscopy image system that is equipped with a digital camera, such as a charge-coupled device (CCD) or complementary metal oxide semiconductor (CMOS) camera.
- Step 4: The digitized images are analyzed using a software that has spot counting and fluorescence intensity detection capability, such as those currently used by interphase qFISH (e.g., Telometer within ImageJ, Isis from MetaSystems Group, Inc., or METAMORPH® from Molecular Devices, LLC).
- Step 5: Generate a standard curve using data from cloned telomere standards (e.g., 200 bp, 600 bp, 2.4 kb, 4.8 kb, 6.0 kb and 9.0 kb) that are included in each plate. A linear regression model ($TL_{bp}=\alpha+\beta TL_{FIU}$) is used to convert fluorescence intensity unit (FIU) into absolute telomere length in bp, based on the $\alpha$ (intercept) and $\beta$ (slope) generated from the standard curve.

Figure 2:
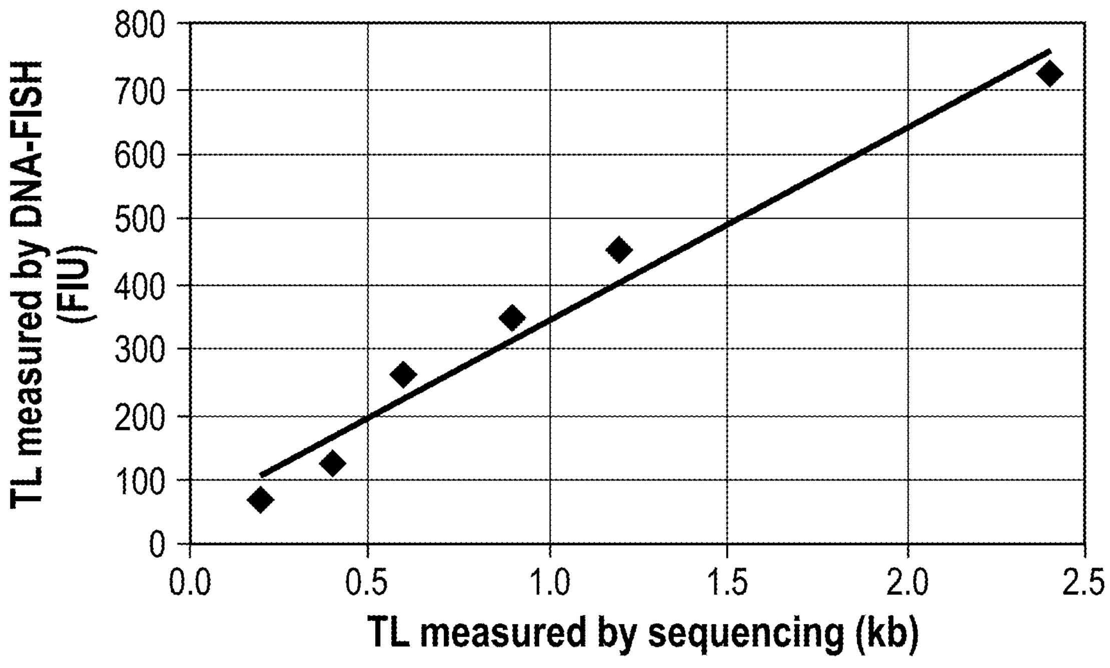
FIG. 2 is a graph depicting correlation of telomere length (TL) of cloned telomere standards as measured by DNA-FISH and by sequencing. FIU, fluorescence intensity units. Spearman correlation coefficient (r)=0.99.

To demonstrate feasibility, telomere lengths of 6 cloned telomere standards that contained 0.2, 0.4, 0.6, 0.9, 1.2, and 2.4 kb telomere fragments, respectively, were measured. FIG. 2 shows that TL measured by DNA-FISH was highly correlated with TL measured by sequencing (Spearman correlation coefficient (r)=0.99). Due to extremely low background signal of DNA-FISH, TL as short as 0.2 kb was readily detectable (FIG. 3A), demonstrating the high-sensitivity of this method. In a separate experiment, 8 pairs of blood DNA samples (DNA purified from PBMCs and granulocytes of the same individual) were analyzed and found that average TL was not significantly different between PBMCs and granulocytes (P=0.45). TLV was observed to be significantly higher in PMBCs than in granulocytes (80.9% vs 74.7%, P=0.025), suggesting that TLV is a more sensitive telomere marker to delineate cell types than average TL.

Example 9. Adoption of 96-Well Format for High-Throughput TL Analysis of DNA Samples This example tests the reproducibility of the DNA-FISH assay using short TL, median TL, and long TL DNA controls. Additionally, the reproducibility and linearity of the method are tested using cloned telomere standards of 0.6 kb, 4.8 kb and 9.0 kb. Key steps of the method, such as amount of input DNA per well, hybridization buffer, telomere PNA probe concentration, DNA denaturation and hybridization conditions, image acquisition conditions (e.g., exposure time, area and distance to be imaged) are vigorously tested and standardized. At the beginning, a mean base value is established from repeated experiments for the standard curve. Large deviations (i.e., values outside the mean±one SD) from the base value of standard curve may indicate poor FISH hybridization, and all the results from such a plate are rejected. Well effects are tested for intra-plate variability by repeated experiments using control DNA samples. Inter-plate variability is tested by repeating the same experiments at different days, weeks, and/or months. The intra-plate and inter-plate coefficients of variation are determined. Depending on the distribution of the data, linear or generalized linear mixed models are used to examine for any intra-plate and inter-plate differences, in that time and well are included as covariates. The intra-class correlation coefficient is calculated to assess the intra-plate and inter-plate variability.

Variations in FISH hybridization efficiency could introduce variability in Q-FISH method, and thus it needs to be tightly controlled. By design, the DNA-FISH method includes cloned telomere standards in each plate. TL is calculated by fitting the testing DNA FIU values against a standard curve, which automatically corrects for hybridization efficiency and improves reproducibility. The image analysis software is tested and refined on large number of images generated from control DNA samples and from cloned telomere standards. Specific criteria are developed to reject poor quality images, such as images that are out of focus or when the density of the telomere signal is too high. The density of telomere signals affects the rate of overlapping telomeres and needs to be tightly controlled. Based on our experience, the optimal number of telomere signals per image is approximately 150-300.

Example 10. Validation

The DNA-FISH method for TL measurement is validated using both the archived sample set (see Example 2) and a control DNA sample set. Pearson or Spearman correlation coefficient is used to compare TL values generated by DNA-FISH and TRF methods. Since DNA-FISH only measures canonical telomere repeats, we anticipate TL measured by DNA-FISH is likely to be shorter than TL measured by TRF, which also contains a polymorphic sub-telomeric region (X region). Both DNA-FISH and TRF measure absolute telomere lengths, thus TL data from these two methods can be compared to estimate the sizes of X region.

Example 11. Preliminary Results

Preliminary results showed that telomeres of 0.2 kb were readily detectable using existing fluorescent microscopy image system that is equipped with a low sensitivity CCD camera (FIG. 3A). A high quality CCD/CMOS camera is expected to increase further the sensitivity to detect telomeres shorter than 0.2 kb. The dynamic range of the assay is similar to that of Q-FISH assays, and is determined by the dynamic range of CCD/CMOS camera for quantitative fluorescent signal detection. For example, the Prime 4 Megapixel backside illuminated (BSI) scientific CMOS camera from Photometrics can detect bright and dim signals with a dynamic range of 35,000:1, which exceeds the dynamic range that is needed to detect TL signals in normal human cells.

Example 12. Potential for Adoption of DNA-FISH for Large Population Studies

DNA-FISH using 96-well microplate or microarray format can assay 41 samples (each sample assayed in duplicate, 14 wells used by telomere standards) per plate run or 150 samples per two microarray slides. One technician can run three plates (123 samples) or 30 microarray slides (2,250 samples) per day. The method uses a commercially available microscopy image system that is commonly used for Q-FISH and cell-based drug screening assays for image acquisition, and thus can easily be adopted by many research labs. Such a system is also moderately priced for purchase from several vendors, e.g., Leica Microsystems, BioVision Technologies Inc. or MetaSystems Inc. The spot counting and fluorescence intensity detection software are available both freely (Telometer within ImageJ, and Flintbox.com) or from commercial vendors (Navigation from Leica Microsystems, Isis from MetaSystems Group, Inc. and METAMORPH® from Molecular Devices, LLC).

Example 13. Measurement of Chromosome-Specific TL

Figure 4A:
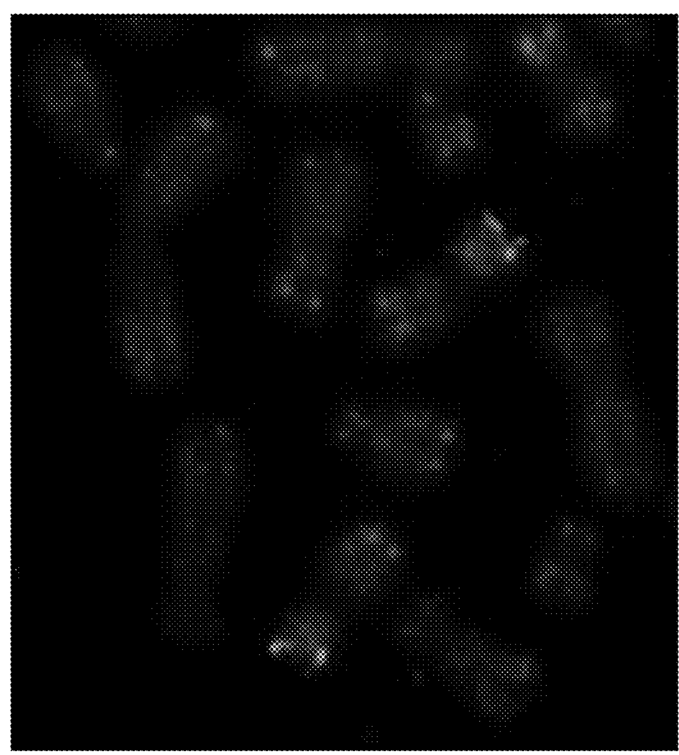
FIG. 4A is a photographic image depicting overlapping chromosome 9p telomere and sub-telomere signals in metaphase chromosomes. Arrows point to representative overlapping signals.
Figure 4B:
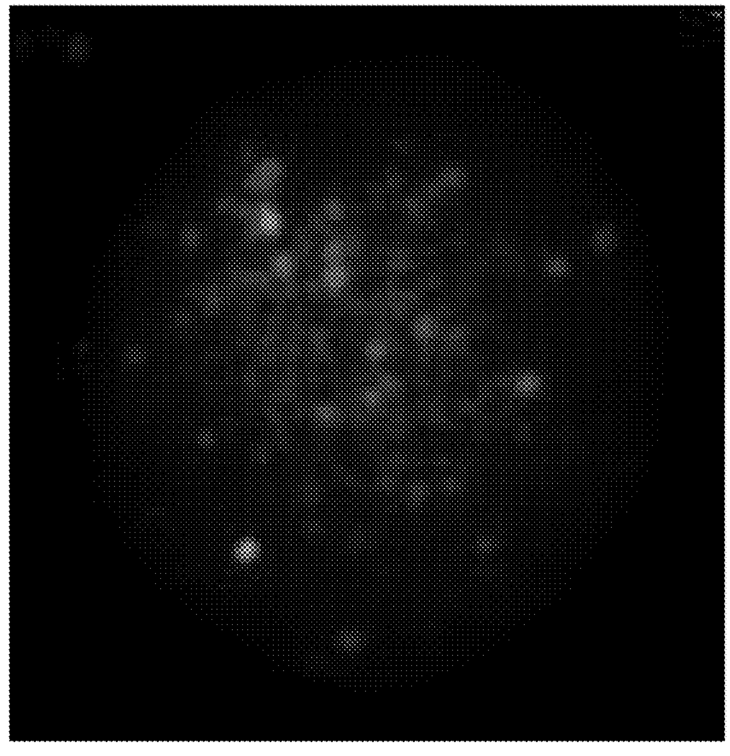
FIG. 4B is a photographic image depicting overlapping telomere and chromosome 9p sub-telomere signals in interphase nuclei. Arrows point to representative overlapping signals.

DNA-FISH has the potential to measure chromosome-specific TL if a sub-telomeric probe is introduced to mark the specific chromosomal arm of interest. As a proof-of-principle, experiments were performed to measure chromosome 9p-specific telomere lengths on metaphase chromosomes and interphase nuclei. A BAC clone (RP11-59O6) containing chromosome 9p sub-telomere sequences (adjacent to telomere) was purchased from the BAC/PAC Resources at Children's Hospital Oakland Research Institute, CA. Purified BAC DNA was labeled with FITC (green signal) and used to mark the chromosome 9p telomere (red signal) in metaphase chromosomes (FIG. 4A) and interphase nuclei (FIG. 4B). FIGS. 4A and 4B are representative pictures showing the overlapping telomere (red) and sub-telomere signals (green) on chromosome 9p. This method allows measuring 4 telomere parameters for a specific chromosomal arm: 1) average TL per telomere; 2) telomere length variation; 3) frequency of short telomeres; and 4) frequency of long telomeres. For example, telomeres on the short arm of chromosome 9 can be marked by a second probe and measured as shown in FIGS. 4A and 4B.

The invention claimed is:

1. A method for determining chromosomal arm specific telomere length, comprising:

a) immobilizing onto a substrate at least one sample of genomic DNA and a plurality of telomere length standards of different lengths;

b) contacting the immobilized genomic DNA and telomere length standards of step a) with a first fluorescently labeled probe having a sequence complementary to a telomere sequence and a second fluorescently labeled probe having a sequence complementary to a unique subtelomeric sequence of a specific chromosomal arm under conditions such that said probes hybridize specifically to telomeric DNA and the unique subtelomeric DNA;

c) detecting hybridized probes with a fluorescent microscopy image system, thereby generating digitized images of the hybridized probes;

d) analyzing the digitized images to identify telomere spots that are marked by subtelomeric probe fluorescent signal and measure the fluorescent intensity of each marked telomere spot;

e) generating a standard curve of telomere length in base-pair versus spot fluorescent intensities based on the plurality of telomere length standards on the substrate; and f) determining base-pair length of each marked telomere molecule (spot) by converting fluorescent intensity of telomere spot into base-pair length using a statistic mode against standard curve.

2. The method of claim 1, wherein:

the genomic DNA is human DNA;

the telomere length standards are cloned telomere fragments or telomere DNA fragments purified from cells; and/or the plurality of telomere length standards of different lengths comprises telomere lengths of about 0.1 to ≥9.0 kb.

3. The method of claim 1, wherein the substrate:

comprises a solid surface;

consists of glass, polymer, film or membrane;

consists of multi-well plates; and/or consists of coated solid surface, wherein the coating is optionally a chemical that is optionally alkoxysilane or aminosilane, or is optionally a biomolecule that is optionally a protein.

4. The method of claim 1, wherein the fluorescent microscopy image system comprises a fluorescent microscope, an automatic stage, a computer equipped with system and specialized software, and a digital camera.

5. The method of claim 4, wherein the digital camera comprises a charge-coupled device or a complementary metal oxide semiconductor camera.

6. The method of claim 1, wherein the statistic model is linear regression.

7. The method of claim 1, further comprising determining the following for each sample of chromosomal arm:

(i) average telomere length per telomere;

(ii) telomere length variation;

(iii) frequency of short telomeres;

(iv) frequency of long telomeres; or (v) any combination thereof.

8. The method of claim 7, wherein:

the short telomeres are less than or equal to about 4 kb long;

the short telomeres are less than or equal to about 1 kb long;

the long telomeres are greater than or equal to about 11 kb long; or the long telomeres are greater than or equal to about 15 kb long.

9. The method of claim 1, wherein:

at least 100 telomeres are analyzed for each chromosomal arm; or about 1000 telomeres are analyzed for each chromosomal arm.

* * * * *